(12) United States Patent
Beyerinck et al.

(10) Patent No.: US 10,383,941 B2
(45) Date of Patent: *Aug. 20, 2019

(54) SPRAY DRYING PROCESSES FOR FORMING SOLID AMORPHOUS DISPERSIONS OF DRUGS AND POLYMERS

(75) Inventors: Ronald Arthur Beyerinck, Bend, OR (US); Daniel Elmont Dobry, Bend, OR (US); Dwayne Thomas Friesen, Bend, OR (US); Dana Marie Settell, Bend, OR (US); Roderick Jack Ray, Bend, OR (US)

(73) Assignee: Bend Research, Inc., Bend, OR (US)

(*) Notice: Subject to any disclaimer, the term of this patent is extended or adjusted under 35 U.S.C. 154(b) by 1433 days.

This patent is subject to a terminal disclaimer.

(21) Appl. No.: 10/910,115

(22) Filed: Aug. 3, 2004

(65) Prior Publication Data

US 2005/0031692 A1 Feb. 10, 2005

Related U.S. Application Data

(60) Provisional application No. 60/492,407, filed on Aug. 4, 2003, provisional application No. 60/568,989, filed on May 7, 2004.

(51) Int. Cl.

| | | |
|---|---|---|
| A61K 45/06 | (2006.01) | |
| A61K 31/56 | (2006.01) | |
| A61K 9/107 | (2006.01) | |
| A61K 9/16 | (2006.01) | |
| A61K 9/48 | (2006.01) | |
| A61K 9/50 | (2006.01) | |
| A61K 31/366 | (2006.01) | |

(Continued)

(52) U.S. Cl.
CPC ............ *A61K 45/06* (2013.01); *A61K 9/0004* (2013.01); *A61K 9/1075* (2013.01); *A61K 9/1652* (2013.01); *A61K 9/1694* (2013.01); *A61K 9/4808* (2013.01); *A61K 9/4858* (2013.01); *A61K 9/5084* (2013.01); *A61K 31/366* (2013.01); *A61K 31/40* (2013.01); *A61K 31/401* (2013.01); *A61K 31/4706* (2013.01); *A61K 31/56* (2013.01)

(58) Field of Classification Search
CPC .... A61K 45/06; A61K 9/1075; A61K 9/1652; A61K 9/1694; A61K 9/4858; A61K 9/5084
USPC .......................................................... 424/489
See application file for complete search history.

(56) References Cited

U.S. PATENT DOCUMENTS

| | | | |
|---|---|---|---|
| 4,056,599 A | 11/1977 | Fox, III et al. | ............... 423/178 |
| 4,187,617 A | 2/1980 | Becker, Jr. et al. | .............. 34/57 |

(Continued)

FOREIGN PATENT DOCUMENTS

| | | |
|---|---|---|
| AU | 2004261061 | 2/2005 |
| CA | 2534129 | 2/2005 |

(Continued)

OTHER PUBLICATIONS

Material Safety Data Sheet (MSDS), "Acetone," Sciencelab.com, pp. 1-7.*

(Continued)

*Primary Examiner* — Rachael E Bredefeld
(74) *Attorney, Agent, or Firm* — Klarquist Sparkman, LLP

(57) ABSTRACT

Spray drying processes are used to form pharmaceutical compositions comprising a solid amorphous dispersion of a drug and a polymer.

8 Claims, 6 Drawing Sheets

(51) Int. Cl.
*A61K 31/40* (2006.01)
*A61K 31/401* (2006.01)
*A61K 9/00* (2006.01)
*A61K 31/4706* (2006.01)

(56) References Cited

U.S. PATENT DOCUMENTS

| | | | |
|---|---|---|---|
| 4,233,114 A | 11/1980 | Gastaldi | 159/4 |
| 5,272,820 A * | 12/1993 | Ito et al. | 34/585 |
| 5,919,408 A | 7/1999 | Muller et al. | 264/5 |
| 6,020,403 A | 2/2000 | Eck et al. | 523/340 |
| 6,068,859 A | 5/2000 | Curatolo et al. | 424/490 |
| 6,194,000 B1 | 2/2001 | Smith et al. | 424/458 |
| 6,197,348 B1 | 3/2001 | Morella et al. | 424/497 |
| 6,253,463 B1 | 7/2001 | Hansen | 34/362 |
| 6,651,898 B2 | 11/2003 | Nowotny et al. | 239/7 |
| 6,711,831 B1 | 5/2004 | Hansen et al. | 34/373 |
| 6,848,197 B2 * | 2/2005 | Chen et al. | 34/373 |
| 2002/0103225 A1* | 8/2002 | Curatolo et al. | 514/313 |
| 2003/0064108 A1 | 4/2003 | Lukas et al. | 424/495 |
| 2003/0086976 A1 | 5/2003 | Hayes et al. | 424/486 |
| 2003/0198674 A1* | 10/2003 | Curatolo et al. | 424/468 |
| 2003/0225104 A1 | 12/2003 | Hayes et al. | 514/254.07 |

FOREIGN PATENT DOCUMENTS

| | | | |
|---|---|---|---|
| EP | 0214441 | 3/1987 | B01D 1/18 |
| EP | 0436373 A1 | 7/1991 | |
| EP | 0492007 | 2/1995 | B01J 13/04 |
| EP | 0400910 | 11/1995 | A61K 7/00 |
| EP | 0901786 | 3/1999 | A61K 9/14 |
| EP | 1027886 | 8/2000 | A61K 9/14 |
| EP | 1027887 | 8/2000 | A61K 9/26 |
| EP | 1027888 | 8/2000 | A61K 9/26 |
| EP | 1653928 | 3/2012 | |
| GB | 475635 | 11/1937 | |
| GB | 1131242 | 10/1968 | B05B 1/34 |
| GB | 1329791 | 9/1973 | B01D 1/18 |
| GB | 2231266 A | 11/1990 | |
| JP | H02295926 | 12/1990 | |
| JP | H05320045 | 12/1993 | |
| JP | 2011016821 | 1/2011 | |
| KR | 20060087501 | 8/2006 | |
| NZ | 544892 | 9/2008 | |
| RU | 2318495 | 3/2008 | |
| WO | WO 9738678 | 10/1997 | A61K 9/16 |
| WO | WO 0064552 A1 | 11/2000 | |
| WO | WO 0168055 | 9/2001 | A61K 9/14 |
| WO | WO 0168092 | 9/2001 | A61K 31/404 |
| WO | WO 03000226 | 1/2003 | A61K 9/00 |
| WO | WO 03063821 | 8/2003 | A61K 9/00 |
| WO | WO03063821 * | 8/2003 | A61K 9/00 |
| WO | WO 03063832 | 8/2003 | A61K 9/16 |
| WO | WO 03063833 | 8/2003 | A61K 9/16 |
| WO | WO2005/011636 | 2/2005 | |

OTHER PUBLICATIONS

Deis, Ronald. "Spray-Drying: Innovative Use of an Old Process," Design Elements, May 1997, pp. 1-7.*
Marshall, W. R. Jr. et al., Chemical Engineering Progress, 46:11, pp. 575-584, 1950.
Marshall, W. R. Jr., Atomization an Spray Drying by W. R. Marshall Jr. American Institute of Chemical Engineers, New York, NY, chapter VI, pp. 50-56, 1954.
Newton, J. M., Manufacturing Chemist and Aerosol News, 37:4, pp. 33-36, 1966.
Shebler, K. J., The Australian Journal of Dairy Technology, 23:3, pp. 131-136, 1970.
Anon, Food Technology in New Zealand, p. 27, Sep. 1972.
Kutcher, P., Winter School on Spray Drying: Papers and Discussions from the Winter School/Conducted by Australian Society of Dairy Technology, pp. 75-81, 1975.
Gauvin, W. H. et al, AIChE Journal, 22:4, pp. 713-724, 1976.
Keey, R. B. et al., The chemical Engineer, Jul./Aug., pp. 516-521, 1976.
Keey, R. B., et al., Chemical Engineering Science, vol. 32, pp. 1219-1226, 1977.
Dittman, F. W., et al., Chemical Engineering, 84:2, pp. 108-112, 1977.
Yates, W. E., et al., Transactions of the ASAE, 26:6, pp. 1638-1643, 1983.
Crowe, C. T., Drying Technology, 1:1, pp. 35-56, 1983-84.
Masters, K., Spray Drying Handbook, 4$^{th}$ ed., George Godwin, London, England, pp. 54-55, 1985.
Masters, K., Spray Drying Handbook, 4$^{th}$ ed., George Godwin, London, England, chapter 7, pp. 263-269, 1985.
Usui, H., et al., Journal of Chemical Engineering of Japan, 18:5, pp. 464-466, 1985.
Hayashi, H., et al., Drying Technology, 4:3, pp. 31-342, 1986.
Zhelev, J. B., Drying Technology, 7:3, pp. 477-485, 1989.
Lefebvre, A. H., Atomization an Sprays, Taylor and Francis Publishers, chapter 4, pp. 105-153, 1989.
Lefebvre, A. H., Atomization and Sprays, Taylor and Francis Publishers, chapter 9, pp. 367-409, 1989.
Ferrazza, G., et al., Chemical Engineering, pp. 177-184, Nov. 1990.
Masters, K., Drying 91, A.S. Mujumdar and I Filkova (eds), Elsevier Science Publishers, Amsterdam, The Netherlands, pp. 56-73, 1991.
Oakley, D. E., et al., Drying 91, A.S. Mujumdar and I. Filkova (eds), Elsevier Science Publishers, Amsterdam, The Netherlands, pp. 303-313, 1991.
Liang, G. et al., Drying Technology, 9:1, pp. 1-25, 1991.
Killeen, J.J., Pharmaceutical Engineering, pp. 56-64, Jul./Aug. 1991.
P. Giunchedi, et al., Journal of Microencapsulation, 11:4, pp. 381-393, 1994.
U. Conte, et al., Drug Development and Industrial Pharmacy, 20:3, pp. 235-258, 1994.
P. Giunchedi, et al., S. T. P. Pharma Sciences, 5:4, pp. 276-290, 1995.
C. Bitz, et al., International Journal of Pharmaceutics, vol. 131, pp. 171-181, 1996.
D. E. Oakley, chemical Engineering Progress, pp. 48-54, Oct. 1997.
S. Wendel et al., Pharmaceutical Technology, pp. 124-156, Oct. 1997.
B. Ertl, et al., Scientia Pharmaceutica, vol. 66, pp. 105-115, 1998.
A. Billon, et al., Drug Development and Industrial Pharmacy, 25:11, pp. 1149-1156, 1999.
B. Baras, et al., International Journal of Pharmaceutics, vol. 200, pp. 133-145, 2000.
E. Esposito, et al., Pharmaceutical Development and Technology, 5:2, pp. 267-278, 2000.
T. Hino, et al., European Journal of Pharmaceutics and Biopharmaceutics, vol. 49, pp. 79-85, 2000.
H. Liu, Science and Engineering of Droplets—Fundamentals and Applications, Noyes publications, Park Ridge, NJ, pp. 19-65, 2000.
Y.-J. Fu, et al., Journal of Microencapsulation, 18:6, pp. 733-747, 2001.
International Preliminary Report on Patentability and Written Opinion for PCT/IB2004/002519 (dated Aug. 10, 2005).
International Search Report for PCT/IB2004/002519 (dated Feb. 3, 2005).
Notification of Reason for Refusal for Korean Patent Application No. 10-2006-7002434 (dated Apr. 27, 2007).
Notification of Reason for Refusal for Korean Patent No. 10-2006-7002434 (dated Feb. 1, 2008).
Notification of Reasons for Refusal for Japanese Patent Application No. 2010-190789 (dated Oct. 10, 2012).
Office Action for European Patent Application No. 047441688 (dated Jul. 3, 2006).
Office Action for European Patent Application No. 047441688 (dated Aug. 27, 2007).

(56) References Cited

OTHER PUBLICATIONS

Office Action for European Patent Application No. 047441688 (dated Aug. 25, 2009).

* cited by examiner

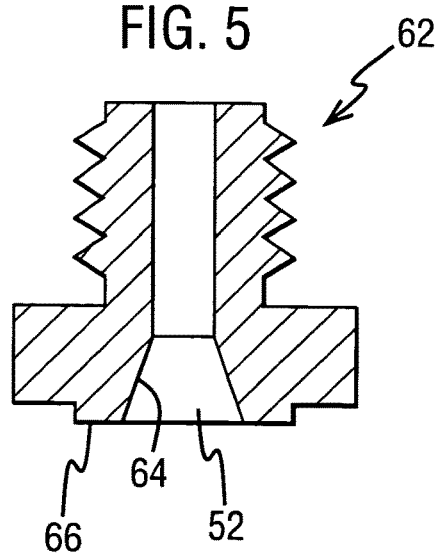
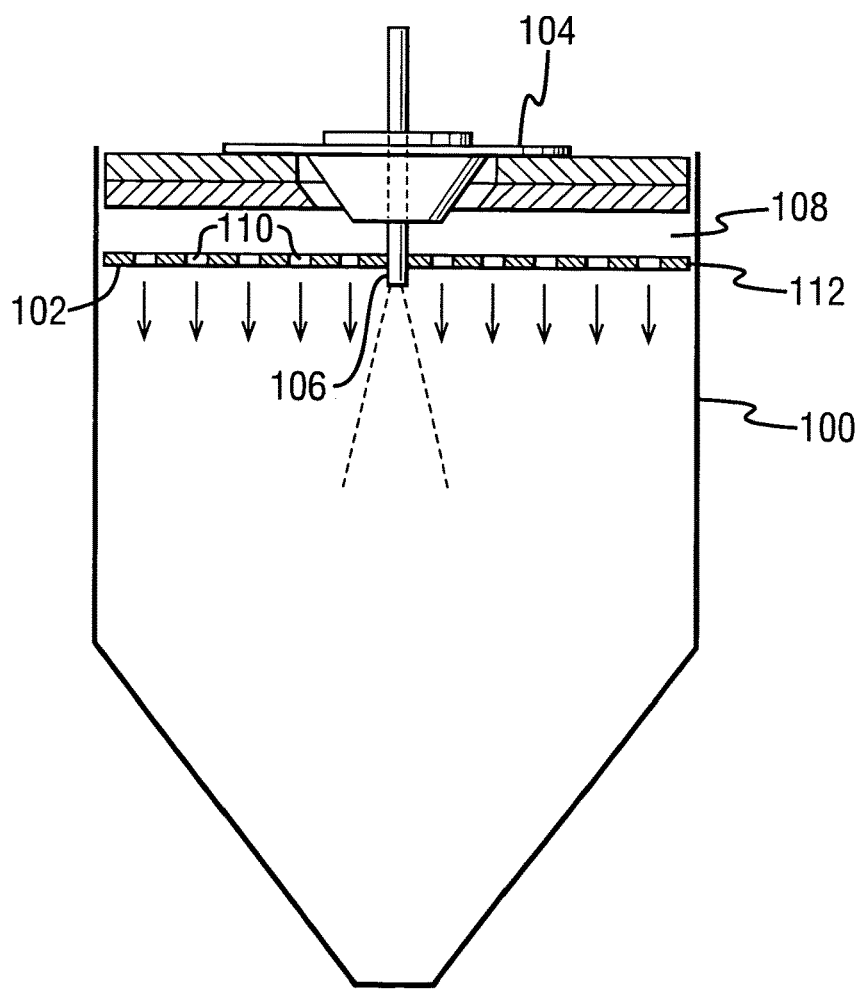

SPRAY DRYING PROCESSES FOR FORMING SOLID AMORPHOUS DISPERSIONS OF DRUGS AND POLYMERS

BACKGROUND OF THE INVENTION

This invention relates to a spray drying process for forming pharmaceutical compositions comprising a solid amorphous dispersion of a low-solubility drug and a polymer.

It is sometimes desired to form a solid amorphous dispersion of a drug and a polymer. One reason for forming solid amorphous dispersions is that the aqueous dissolved drug concentration of a poorly aqueous soluble drug may be improved by forming an amorphous dispersion of the drug and a polymer. For example, Curatolo et al., EP 0 901 786 A2 disclose forming pharmaceutical spray-dried dispersions of sparingly soluble drugs and the polymer hydroxypropyl methyl cellulose acetate succinate. Such solid amorphous dispersions of drug and polymer provide higher concentrations of dissolved drug in an aqueous solution compared with the drug in crystalline form. Such solid amorphous dispersions tend to perform best when the drug is homogeneously dispersed throughout the polymer.

While spray drying processes are well known, spray drying solid amorphous dispersions provides a number of unique challenges. Spray drying involves dissolving the drug and polymer in a solvent to form a spray solution, atomizing the spray solution to form droplets, and then rapidly evaporating the solvent from the droplets to form the solid amorphous dispersion in the form of small particles. The solid amorphous dispersion particles are preferably homogeneous, solid dispersions of amorphous drug in the polymer. Often, it is desirable for the amount of drug in the solid amorphous dispersion to be greater than the solubility of the drug in the polymer (in the absence of the solvent), while still having the drug homogeneously dispersed in the polymer rather than separated into drug-rich domains. Such homogeneous solid amorphous dispersions are termed "thermodynamically unstable." To form such dispersions by spray drying, the solvent must be evaporated rapidly from the spray solution droplets, thereby achieving a homogeneous solid amorphous dispersion. However, rapid evaporation of solvent tends to lead to particles that are either very small, have very low density (high specific volume), or both. Such particle properties can lead to difficulties handling the material and formation of dosage forms containing the solid amorphous dispersion particles.

In contrast, drying conditions that tend to favor larger, denser particles may result in other problems. First, slow evaporation of the solvent from the spray solution droplets may allow the drug to separate from the polymer during evaporation of the droplets, leading to non-homogeneous, phase-separated dispersions. That is, the solid dispersion contains a drug-rich phase and a polymer-rich phase. Second, drying conditions that favor large, dense particles can result in high levels of residual solvent in the solid amorphous dispersion. This is undesirable for at least two reasons. First, high residual solvent levels in the solid amorphous dispersion particles can result in non-homogeneous dispersions in which the drug phase separates from the polymer. Second, as the amount of residual solvent increases, the product yield from spray drying decreases due to incomplete drying of the droplets, which allows the damp droplets to stick to various portions of the dryer. Polymer and drug that stick to the dryer surfaces not only lowers yields, but can break loose from the surface and be present in the product as large, non-homogeneous particles or chunks. Such material often has higher levels of impurities if the material is exposed to high temperatures for longer times than the majority of the spray dried material.

In addition, the production of large quantities of solid amorphous dispersion particles for commercial purposes requires that large volumes of solvent must be used. The process used to spray dry large quantities of spray solution must be capable of balancing the need to rapidly evaporate solvent to form homogeneous solid amorphous dispersions with the need to form particles that have the desired levels of residual solvent and handling characteristics.

Finally, it is often desirable to utilize a drying gas such as nitrogen that is inert and reduces the potential for fire or explosions. It is desirable to minimize the use of such gases due to cost as well as minimize the amount of solvent discharged as vapor in such gases following use.

Accordingly, there is still a need for a spray drying process to prepare pharmaceutical compositions of solid amorphous dispersions comprising low-solubility drugs and polymers that is capable of providing large quantities of spray dried solid amorphous dispersions that are homogeneous, are dense, and have low residual solvent content.

BRIEF SUMMARY OF THE INVENTION

In one aspect, a process is provided for forming a pharmaceutical composition comprising a solid amorphous dispersion comprising a drug and a polymer, comprising the following steps. A drying apparatus is provided having an atomizer connected to a drying chamber, the drying chamber having an inlet and an outlet. A spray solution is formed by dissolving the low-solubility drug and the polymer in a solvent. (The low-solubility drug has low solubility in aqueous solutions as defined below.) The spray solution is sprayed through the atomizer into the chamber to form droplets having a volume average size of less than 500 µm. A drying gas is flowed through the inlet at a flow rate and a temperature $T_{IN}$ such that the droplets solidify in less than about 20 seconds. The feed rate of the spray solution is at least 10 kg/hr, and the feed rate of the spray solution and the $T_{IN}$ of the drying gas are controlled so that the drying gas at the outlet has a temperature $T_{OUT}$ that is less than the boiling point of the solvent.

The inventors have found that while the properties of the spray dried dispersion can vary greatly depending on the spray drying conditions, nevertheless the temperature of the exhaust drying gas at the outlet, or $T_{OUT}$, appears to be critical to producing solid amorphous dispersions that are homogeneous, have low residual solvent, and are dense. Thus, when scaling up the spray drying process to larger volumes of spray solution and larger volumes of drying gas, the flow rates of each should be controlled so as to maintain $T_{OUT}$ at less than the boiling point of the solvent.

The inventors have found that to form solid amorphous dispersions that are substantially homogeneous, that are dense, and that have low residual solvent levels, it is desired to spray dry the spray solution under conditions that are relatively cool and dry. Thus, the present invention contrasts with conventional spray drying methods that employ hot drying conditions to rapidly evaporate the solvent. Conventionally, to maximize the production of product from a spray drying apparatus, the spray solution is fed into the apparatus at the limit of the capacity of the drying apparatus. Since the drying gas flow rate is constrained by the drying apparatus, the drying gas is heated to very hot temperatures to provide sufficient energy to evaporate the solvent. As discussed in greater detail below, the inventors have found that the conventional hot spray drying conditions are not conducive to producing solid amorphous dispersions that are homogeneous, dense, and have low residual solvent. Instead, the drying gas inlet temperature and spray solution feed rate should be controlled to maintain relatively cool conditions in the drying chamber, as determined by the temperature of the drying gas at the outlet, $T_{OUT}$. In addition, the conditions are chosen to be dry; that is, have a sufficient excess of drying gas to solvent in the drying chamber, so that the solvent rapidly evaporates notwithstanding the lower drying gas temperature at the inlet $T_{IN}$. One of the resulting advantages of the present process is that it results in a homogeneous solid amorphous dispersion with a higher drug to polymer ratio than is possible with conventional manufacturing methods.

In another aspect, a process is provided for forming a pharmaceutical composition comprising a solid amorphous dispersion comprising a drug and a polymer, comprising the following steps. A drying apparatus is provided having an atomizer connected to a drying chamber, the drying chamber having an inlet and an outlet. A spray solution is formed by dissolving the low-solubility drug and the polymer in a solvent. The spray solution is sprayed through the atomizer into the chamber to form droplets having a volume average size of less than 500 μm. A drying gas is flowed through the inlet at a flow rate and a temperature $T_{IN}$ such that the droplets solidify in less than about 20 seconds. The drying gas entering the inlet further comprises the solvent in vapor form. In a preferred embodiment of this aspect, the drying gas exiting the drying chamber from the outlet is recirculated to the inlet through a solvent collection system, and the solvent collection system removes only a portion of the solvent from the drying gas prior to reentry of the drying gas into the inlet.

In another aspect of the invention, $T_{OUT}$ is between 5 and 25° C. less than the boiling point of the solvent, and more preferably $T_{OUT}$ is between 10 and 20° C. less than the boiling point of the solvent.

In another aspect, $T_{OUT}$ is less than the glass transition temperature of the solid amorphous dispersion at the residual solvent level of the solid amorphous dispersion as it exits the drying chamber.

In another aspect, the dewpoint of the solvent in the drying chamber is substantially lower than $T_{OUT}$, and may be at least 10° C., at least 20° C., or even at least 30° C. less than $T_{OUT}$.

In another aspect of the invention, the spray solution is formed by mixing the low-solubility drug, polymer and the solvent in a separate mixing device such as powder disperser.

In another aspect of the invention, the atomizer is a pressure nozzle. In one embodiment, the pressure nozzle defines an inner conical surface adjacent to the exit orifice of the nozzle to reduce the build-up of dried material on the nozzle.

In another aspect of the invention, the spray solution has a high feed rate. The feed rate may be at least 50 kg/hr, at least 100 kg/hr, or even at least 200 kg/hr. In one embodiment, the spray solution feed rate is at least 400 to 600 kg/hr.

The foregoing and other objectives, features, and advantages of the invention will be more readily understood upon consideration of the following detailed description of the invention.

FIG. 5 is a cross-sectional view of the nozzle body of FIG. 4.

FIG. 6 is a schematic view of a gas disperser.

DETAILED DESCRIPTION OF THE INVENTION

Figure 1:
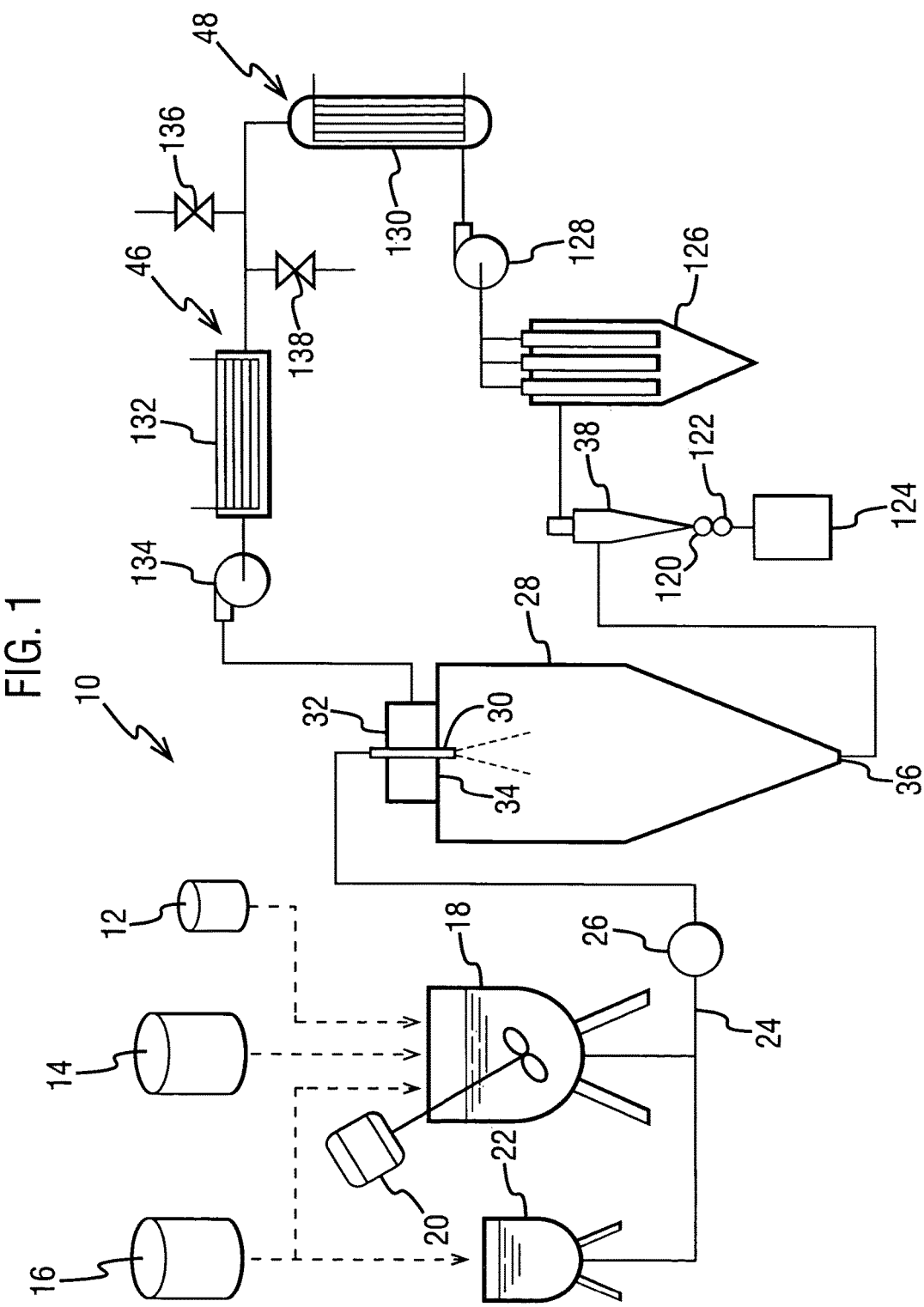
FIG. 1 is a schematic drawing of a spraying drying system.

The present invention relates to spray-drying processes for forming pharmaceutical compositions comprising homogeneous solid amorphous dispersions of a low-solubility drug and a polymer, and in particular to processes for spray-drying large volumes of a spray solution to form solid amorphous dispersions in large quantities. In the present process, homogeneous, solid amorphous dispersions are formed by first dissolving the low-solubility drug and polymer in a solvent to form a spray solution. The solvent is then rapidly removed to form a solid amorphous dispersion.

The concentration of drug in the resulting dispersion formed by the process disclosed herein may be below the solubility of the drug in the polymer (at room temperature). Such dispersions are termed thermodynamically stable dispersions and are normally homogeneous; that is, the drug is substantially homogeneously dispersed in the polymer at the molecular level and thus can be viewed as a solid solution.

Often, it is desirable to form dispersions where the concentration of drug in the polymer is in excess of its solubility but still homogeneous. Such dispersions are termed thermodynamically unstable. The key to forming homogeneous solid amorphous dispersions that are thermodynamically unstable is to rapidly remove the solvent. If the solvent is removed from the spray solution on a time scale that is faster than the time scale at which the drug and polymer phase separate from the spray solution as solvent evaporates, then homogeneous solid amorphous dispersions may be formed even though the concentration of drug in the polymer is above its solubility and is therefore thermodynamically unstable. However, the rate at which the solvent is removed greatly affects the physical properties of the resulting solid amorphous dispersions. The desired properties of solid amorphous dispersions, and the spray-drying conditions needed to achieve these properties are described in more detail below.

Solid Amorphous Dispersions

I. Desired Properties of Solid Amorphous Dispersions

In order to achieve concentration enhancement of the low-solubility drug in an aqueous use environment, the solid amorphous dispersion should have several properties. An aqueous use environment may be either an in vitro use environment, such as a dissolution test media, or an in vivo use environment, such as the GI tract. The degree of concentration enhancement of dissolved drug is described in more detail below, but in general the dispersion, when administered to an aqueous use environment, provides at least temporarily a dissolved drug concentration in the use environment that is greater than the solubility of the crystalline form of the drug in the use environment. Solid amorphous dispersions which provide concentration enhancement in a use environment have the following characteristics: (1) the solid dispersion is "substantially homogeneous"; (2) the drug is "substantially amorphous";

(3) the solid dispersion has a relatively high drug loading; and (4) the solid dispersion has a low residual solvent content.

1. Substantially Homogeneous

As used herein, "substantially homogeneous" means that the drug present in relatively pure amorphous domains within the solid amorphous dispersion is relatively small, on the order of less than 20%. Preferably the amount of drug present in pure amorphous domains is less than 10% of the total amount of drug. In substantially homogeneous dispersions, the drug is dispersed as homogeneously as possible throughout the polymer and can be thought of as a solid solution of drug dispersed in the polymer(s). While the dispersion may have some drug-rich domains, it is preferred that the dispersion itself have a single glass transition temperature ($T_g$) which demonstrates that the dispersion is substantially homogeneous. This contrasts with a simple physical mixture of pure amorphous drug particles and pure amorphous polymer particles which generally display two distinct $T_g$s, one that of the drug and one that of the polymer. $T_g$ as used herein is the characteristic temperature where a glassy material, upon gradual heating, undergoes a relatively rapid (e.g., 10 to 100 seconds) physical change from a glass state to a rubber state.

In order to maintain the homogeneity of the solid amorphous dispersion over time, it is desired that the $T_g$ of the solid amorphous dispersion is greater than the ambient storage temperature. The mobility of the drug in the solid amorphous dispersion is dependent on the $T_g$ of the solid amorphous dispersion. Mobility refers to the capacity of the drug to diffuse through the solid material. When the mobility of the drug in the solid amorphous dispersion is high, the drug may phase separate from the homogeneous solid solution of drug and polymer to form separate drug rich domains. Such drug rich domains may in turn crystallize. In such cases, the resulting non-homogeneous dispersions tend to provide lower concentrations of dissolved drug in an aqueous solution and lower bioavailability relative to homogeneous solid amorphous dispersions. The mobility of the drug is dramatically reduced when the $T_g$ of the solid amorphous dispersion is above the ambient temperature. In particular, it is preferable that the $T_g$ of the solid amorphous dispersion is at least 40° C. and preferably at least 60° C. Since the $T_g$ is a function of the water and solvent content of the solid amorphous dispersion which in turn is a function of the relative humidity (RH) to which the solid amorphous dispersion is exposed, these $T_g$ values refer to the $T_g$ of the solid amorphous dispersion containing water in an amount that is in equilibrium with the RH equivalent to that found during storage. Preferably, the $T_g$ of the solid amorphous dispersion is at least 40° C. and preferably at least 60° C. measured at 50% RH. When the drug itself has a relatively low $T_g$ (about 70° C. or less) it is preferred that the dispersion polymer has a $T_g$ of at least 40° C. at 50% RH, preferably at least 70° C. and more preferably greater than 100° C.

2. Substantially Amorphous

In addition, the drug in the dispersion is "substantially amorphous." As used herein, "substantially amorphous" means that the amount of the drug in amorphous form is at least 75 wt %; that is, the amount of crystalline drug present does not exceed about 25 wt %. More preferably, the drug in the dispersion is "almost completely amorphous," meaning that at least 90 wt % of the drug is amorphous, or that the amount of drug in the crystalline form does not exceed 10 wt %. Amounts of crystalline drug may be measured by powder X-ray diffraction, Scanning Electron Microscope (SEM) analysis, differential scanning calorimetry (DSC), or any other standard quantitative measurement.

To obtain the maximum level of dissolved drug concentration and bioavailability enhancement, particularly upon storage for long times prior to use, it is preferred that the drug remain, to the extent possible, in the amorphous state. The inventors have found that this is best achieved when the glass-transition temperature, $T_g$, of the solid amorphous dispersion is substantially above the storage temperature of the dispersion as described above.

3. Amount of Drug

In order to reduce the amount of inactive material to be dosed, it is usually desired that the drug is present in the solid amorphous dispersion in an amount that is as great as possible while still achieving a dispersion that performs well (e.g., enhances dissolved drug concentration in a use environment and bioavailability when dosed to an animal, such as a mammal). The amount of drug relative to the amount of polymer present in the solid amorphous dispersions of the present invention depends on the drug and polymer. Often, the amount of drug present is greater than the solubility of the drug in the polymer. The present invention allows the drug to be present in the solid amorphous dispersion at a level greater than its solubility in the polymer while still being homogeneously dispersed. The amount of drug may vary widely from a drug-to-polymer weight ratio of from 0.01 to about 49 (e.g., 1 wt % drug to 98 wt % drug). However, in most cases it is preferred that the drug-to-polymer ratio is at least about 0.05 (4.8 wt % drug), more preferably at least 0.10 (9 wt % drug), and even more preferably at least about 0.25 (20 wt % drug). Higher ratios may be possible depending on the choice of drug and polymer, such as at least 0.67 (40 wt % drug). However, in some cases, the degree of concentration-enhancement decreases at high drug loadings, and thus the drug-to-polymer ratio may for some dispersions be less than about 2.5 (71 wt % drug), and may even be less than about 1.5 (60 wt % drug).

In addition, the amount of drug and polymer in the dispersion is preferably high relative to other excipients. Collectively, the drug and polymer preferably comprise at least 80 wt % of the dispersion, and may comprise at least 90 wt %, and up to 100 wt % of the solid amorphous dispersion.

4. Low Residual Solvent Content

The solid amorphous dispersions also have a low residual solvent content. By residual solvent content is meant the amount of solvent present in the solid amorphous dispersion following spray-drying immediately upon exit from the spray dryer. The presence of solvent in the dispersion lowers the glass transition temperature of the dispersion. Thus, mobility of the drug in the dispersion, and hence its propensity to phase separate and crystallize, decreases as the amount of residual solvent in the solid amorphous dispersion decreases. Generally, the residual solvent content of the solid amorphous dispersion should be less than about 10 wt %, preferably less than about 5 wt %, and even more preferably less than 3 wt %.

II. Desired Size and Density of Dispersions

In addition to the properties described above, it is also desired that the solid amorphous dispersions have certain characteristics to facilitate handling and processing. The dispersions should have the following characteristics to facilitate handling: (1) the dispersions should not be too small; and (2) the dispersions should be dense.

1. Size

In general, the solid amorphous dispersions formed by spray drying exit the drying chamber as small particles. While the small particle size may in some cases aid dissolution performance, very small particles, particularly fines (e.g., less than about 1 μm in diameter), can be difficult to handle and process. In general, the mean size of the particles should be less than 500 μm in diameter, and is more preferably less than 200 μm in diameter, and even more preferably less than 100 μm in diameter. A preferred range of mean particle diameter is from about 1 to about 100 μm, and more preferably from about 5 to about 80 μm. Particle size may be measured using conventional techniques, such as by using a Malvern laser light scattering apparatus.

Preferably, the solid amorphous dispersions have a relatively narrow size distribution so as to minimize the fraction of particles that are very small (less than 1 μm). The particles may have a Span of less than or equal to 3, and more preferably less than or equal to about 2.5. As used herein, "Span," is defined as $$\text{Span} = \frac{D_{90} - D_{10}}{D_{50}},$$

where $D_{10}$ is the diameter corresponding to the diameter of particles that make up 10% of the total volume containing particles of equal or smaller diameter, $D_{50}$ is the diameter corresponding to the diameter of particles that make up 50% of the total volume containing particles of equal or smaller diameter, and $D_{90}$ is the diameter corresponding to the diameter of particles that make up 90% of the total volume containing particles of equal or smaller diameter.

2. Density

The particles should also be sufficiently dense so as to facilitate handing and post processing in unit operations such as dry blending, wet or dry granulations, capsule filling, or compression into tablets. The solid amorphous dispersion particles should have a density that is at least 0.1 g/cc. Density may be measured by collecting a representative sample, determining the mass, and then determining the volume of the sample in a graduated cylinder. Preferably, the particles have a density of at least 0.15 g/cc, and more preferably greater than 0.2 g/cc. In other words, the bulk specific volume of the particles should be no more than 10 cc/g, preferably less than 6.7 cc/g and preferably less than 5 cc/g. The particles may have a tapped specific volume of less than or equal to about 8 cc/g, more preferably less than 5 cc/g, and even more preferably less than or equal to about 3.5 cc/g. The particles may have a Hausner ratio of less than or equal to about 3, and more preferably less than or equal to about 2. (The Hausner ratio is the ratio of the bulk specific volume divided by the tapped specific volume.)

Process for Spray Drying

The term spray-drying is used conventionally and broadly refers to processes involving breaking up liquid mixtures into small droplets (atomization) and rapidly removing solvent from the droplets in a container where there is a strong driving force for evaporation of solvent. An exemplary spray-drying system 10 is shown schematically in FIG. 1. The spray-drying system 10 includes tanks or hoppers for drug 12, polymer 14 and solvent 16. The system 10 includes a tank 18 for mixing the spray solution using a mixer 20. The spray solution contains the dissolved drug and polymer in the solvent. An optional solvent tank 22 may be employed to aid in processing. The tank 18 is connected via a feedline 24 having a pump 26 to the drying chamber 28. The feed line 24 is connected to an atomizer 30 located at the top of the chamber 28. The atomizer 30 breaks the spray solution up into fine droplets in the drying chamber 28. A drying gas, such as nitrogen, is also introduced into the chamber through a gas disperser 32. The drying gas enters the drying chamber 28 at an inlet 34. The solvent evaporates from the droplets within the chamber 28, forming solid amorphous dispersion particles of drug and polymer. The solid amorphous dispersion particles and exhaust drying gas (the now cooled drying gas and evaporated solvent) exit the drying chamber 28 out of an outlet 36 at the bottom of the drying chamber 28. The solid amorphous dispersion particles may be separated from the exhaust gas by means of a cyclone 38, or other collection device.

The spray solution and drying conditions must be chosen to balance a variety of factors. First, the spray solution and drying conditions should result in substantially homogeneous solid amorphous dispersions having the physical characteristics described above. Second, the spray solution and drying conditions should also allow efficient manufacture of such dispersions at large volumes of spray solution. The characteristics of the spray solution and drying conditions needed to achieve these two goals are described in more detail below.

I. Spray Solution

The spray solution determines the drug loading of the resulting solid amorphous dispersion, and also affects whether the solid amorphous dispersion is homogeneous and the efficiency of production of the dispersions. The spray solution contains at least the drug, polymer and solvent.

1. Amount of Drug and Polymer

The relative amounts of drug and polymer dissolved in the solvent are chosen to yield the desired drug to polymer ratio in the resulting solid amorphous dispersion. For example, if a dispersion having a drug to polymer ratio of 0.33 (25 wt % drug) is desired, then the spray solution comprises 1 part drug and 3 parts polymer dissolved in the solvent.

The total dissolved solids content of the spray solution is preferably sufficiently high so that the spray solution results in efficient production of the solid amorphous dispersions. The total dissolved solids content refers to the amount of drug, polymer and other excipients dissolved in the solvent. For example, to form a spray solution having a 5 wt % dissolved solids content and which results in a solid amorphous dispersion having a 25 wt % drug loading, the spray solution would comprise 1.25 wt % drug, 3.75 wt % polymer and 95 wt % solvent. The drug may be dissolved in the spray solution up to the solubility limit; however, the amount dissolved is usually less than 80% of the solubility of drug in the solution at the temperature of the solution prior to atomization. The dissolved solids content may range from 0.2 wt % to 30 wt % depending on the solubility of the drug and polymer in the solvent. For drugs having good solubility in the solvent, the spray solution preferably has a solids content of at least 3 wt %, more preferably at least 5 wt %, and even more preferably at least 10 wt %. However, the dissolved solids content should not be too high, or else the spray solution may be too viscous to atomize efficiently into small droplets. The spray solution viscosity may range from about 0.5 to about 50,000 cp, and more typically 10 to 2,000 cp.

2. Solvent Choice

Second, the solvent is chosen to yield a substantially homogenous dispersion having a low residual solvent level. The solvent is chosen based on the following characteristics: (1) the drug and polymer both are soluble, and preferably have high solubility, in the solvent; (2) the solvent is relatively volatile; and (3) the solution gels during solvent removal. Preferably, the solubility of the drug in the solution is high enough so that the drug remains soluble at the solids content at which the solution gels.

a. Solubility Characteristics

In order to achieve dispersions that are almost completely amorphous and substantially homogeneous, the solvent yields a spray solution in which the polymer and drug are both soluble and preferably highly soluble. The drug and polymer should preferably be fully dissolved in the solvent in the spray solution prior to atomization. This allows intimate mixing of the polymer, drug and solvent at the molecular level. Preferably, the drug has a solubility in the solvent at 25° C. of at least 0.5 wt %, preferably at least 2.0 wt % and more preferably at least 5.0 wt %.

The polymer should be highly soluble in the solvent as well. However, for polymers, this is best indicated by the nature of the solution it forms. Ideally, a solvent is chosen that solvates the polymer sufficiently that the polymer is not highly aggregated and forms a visibly clear solution. Polymer aggregation is indicated by the solution being cloudy or turbid when aggregation is high, and by the solution scattering large amounts of light. Thus, the acceptability of a solvent can be determined by measuring the turbidity of the solution or the level of light scattering as is well known in the art. For example, for the polymer hydroxypropylmethyl cellulose acetate (HPMCAS), acetone is a good solvent choice, forming a clear solution when the polymer is, dissolved. In contrast, pure ethanol is a poor choice for HPMCAS at practical dissolved solids content, since only a small portion (about 20 to 30 wt %) of the HPMCAS is soluble in ethanol. This is demonstrated by the nature of the resulting heterogeneous mixture that results when using ethanol as the solvent: a clear solution above an opaque solution of gelled, undissolved polymer. Good salvation also leads to another related property described below, namely gellation. If solvation is poor, the polymer precipitates (separates into a solvent-poor solid and a polymer-poor solution) rather than gelling, that is, remaining as a highly viscous liquid or solid single-phase (polymer and solvent) material.

Solvents suitable for spray-drying can be any compound in which the drug and polymer are mutually soluble. Preferred solvents include alcohols such as methanol, ethanol, n-propanol, iso-propanol, and butanol; ketones such as acetone, methyl ethyl ketone and methyl iso-butyl ketone; esters such as ethyl acetate and propylacetate; and various other solvents such as acetonitrile, methylene chloride, toluene, THF, cyclic ethers, and 1,1,1-trichloroethane. Lower volatility solvents such as dimethyl acetamide or dimethylsulfoxide can also be used. Mixtures of solvents, such as 50% methanol and 50% acetone, can also be used, as can mixtures with water as long as the polymer and drug are sufficiently soluble to make the spray-drying process practicable. In some cases it may be desired to add a small amount of water to aid solubility of the polymer in the spray solution.

b. Boiling Point

To achieve rapid solvent removal, and to keep the residual solvent level in the resulting solid amorphous dispersion low (preferably less than about 5 wt %), a relatively volatile solvent is chosen. Preferably the boiling point of the solvent is less than about 200° C., more preferably less than about 150° C., and more preferably less than about 100° C. When the solvent is a mixture of solvents, up to about 40% of the solvent may comprise a low volatility solvent. Preferably, in such a mixture the boiling point of the other component is low (e.g., less than 100° C.). The boiling point for solvent blends may be determined experimentally. However, if the solvent is too volatile, the solvent will evaporate too rapidly, resulting in particles that have low density unless the evaporation step is conducted at a low temperature. Operation at conditions where the temperature of the exhaust drying gas at the outlet ($T_{OUT}$) is less than about 20° C. is often impractical. In practice, acetone (56° C. boiling point) and methanol (65° C. boiling point) work well for a variety of drugs.

c. Gelling

The solvent is chosen to preferably cause the atomized droplets of drug, polymer and solvent to gel prior to solidification during the evaporation process. Initially, the spray solution is a homogeneous solution of dissolved drug and polymer in the solvent. When the spray solution is sprayed into the drying chamber, the spray solution is atomized into liquid droplets. The solvent begins to rapidly evaporate from the liquid droplets, causing the concentration of the dissolved drug and polymer to increase in the droplet. As the solvent continues to evaporate, there are three possible scenarios: (1) the polymer concentration in the droplet exceeds the gel point of the polymer so as to form a homogeneous gel; (2) the concentration of the dissolved drug in the droplet exceeds the solubility of the drug in the solution in the droplet, causing the drug to phase separate from the solution; or (3) the concentration of the polymer in the droplet exceeds the solubility of the polymer in the solution in the droplet, causing the polymer to phase separate from the solution. Homogeneous solid amorphous dispersions are most easily formed when the solvent and concentrations of polymer and drug are chosen such that, as solvent is evaporated, the polymer, drug and solvent form a homogeneous gel prior to the drug phase separating or the polymer precipitating. In contrast, if the drug or polymer phase separate prior to the polymer gelling, then it becomes more difficult to choose spray drying conditions which will yield a substantially homogeneous dispersion. Gelation of the solution prior to reaching the solubility limit of the drug greatly slows the drug phase separation process, providing adequate time for solidification of the particles in the spray-drying process without significant phase separation.

By choosing a solvent which causes the polymer to gel, the concentration of the polymer will exceed the gel point of the polymer as the solvent evaporates from the solvent, resulting in a homogeneous gel of the drug, polymer and solvent. When this occurs, the viscosity of the solution in the droplet increases rapidly, immobilizing the drug and polymer in the droplet notwithstanding the presence of the solvent. As additional solvent is removed, the drug and polymer remain homogeneously distributed throughout the droplet, resulting in a substantially homogeneous solid dispersion.

Alternatively, the solvent and polymer and drug concentrations may be chosen such that, as the solvent evaporates, the drug concentration exceeds the drug solubility in the solvent—that is supersaturates. In such a case, the drug has a relatively low solubility in the solvent, but the polymer has a high solubility and gels at the saturation point. Such a system may yield a satisfactory solid amorphous dispersion (e.g., the drug is not phase separated as amorphous or crystalline drug) so long as the time during which the solution has a drug concentration above the point where it will ultimately phase separate from the solution (e.g., supersaturated) but is still liquid (e.g., not yet solid) is sufficiently short, that the drug does not substantially phase separate.

3. Solution Mixing

It is important that the spray solution is prepared so as to achieve a homogeneous spray solution in which all of the drug and polymer are completely dissolved. In general, the drug and polymer are added to the solvent and mechanically mixed or agitated over a period of time. Exemplary mixing processes include submerged impellers or agitators. The solution is preferably mixed for a relatively long period of time, such as from four to eight hours, to ensure that all of the polymer and drug have dissolved.

In a preferred embodiment, the drug and polymer are mixed with the solvent using a separate mixing device, such as a high shear powder disperser, jet mixer, or line blender. The inventors found that one problem that may result in forming large batches of the spray solution (greater than about 100 liters) is the failure of the polymer to completely dissolve in the solvent in a reasonable amount of time. If the polymer powder is not well dispersed or if it is added too quickly to the solvent, the polymer may clump and begin to dissolve. Solvent will begin to solvate the outer layer of polymer, forming a gel. Once an outer layer of gel has formed, it becomes more difficult for the solvent to penetrate through the gel layer into the inner layers of dry polymer. Such partially solvated clumps may interfere with the spray-drying process, such as by causing the atomizer to clog. In addition, such clumps may yield non-homogeneous particles, most consisting of a higher drug to polymer ratio than desired, and some particles having a lower drug to polymer ratio than desired. In extreme cases some particles may even consist mostly of polymer. To eliminate this problem, the polymer may be mixed with the drug separately from the tank containing the spray solution, such as by using a high shear powder disperser.

Figure 2:
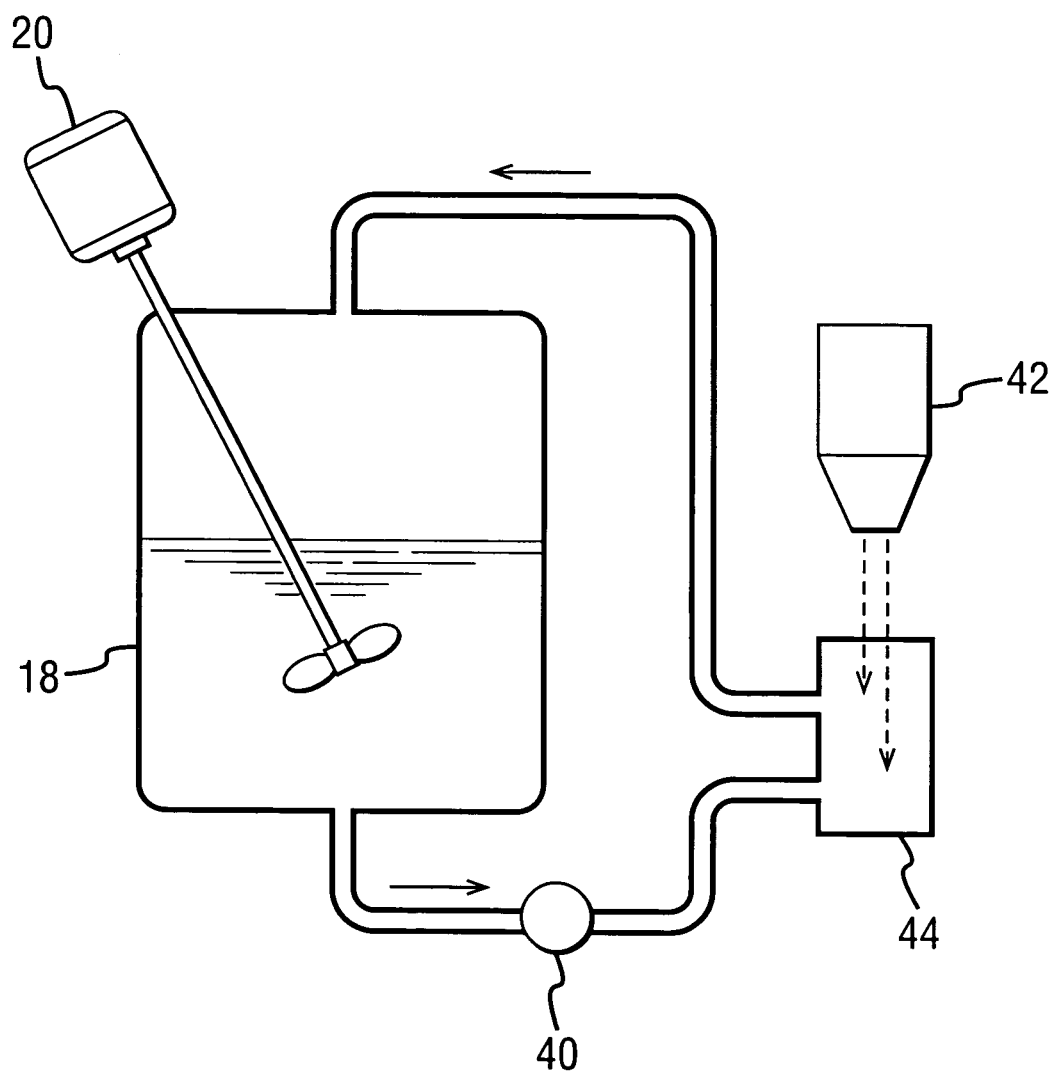
FIG. 2 is a schematic drawing of a mixing system.

FIG. 2 shows schematically a mixing system comprising the solution tank 18, a pump 40, a hopper 42, and a separate mixing device 44. The solution tank 18 initially contains solvent, which is pumped via pump 40 to the mixing device 44. Dry powder material, either drug, polymer or both, is fed through hopper 42 into the device 44. The mixing device 44 combines the solvent and dry material using sufficient mechanical agitation and/or shear to form a homogeneous solution of dissolved drug and polymer, which is then fed into the tank 18. Exemplary separate mixing devices include high shear powder dispersers available from Quadro Engineering incorporated; Waterloo, Ontario, Canada; Silverson Machines Inc.; East Longmeadow, Mass.; LIGHTNIN; Rochester, N.H.; and EKATO Corporation; Ramsey, N.J.

II. Evaporation of Solvent

1. Process Conditions

The manner in which the solvent is evaporated from the spray solution also affects the density and size of the solid amorphous dispersion particles, as well as whether the solid amorphous dispersion is homogeneous. The difficulty in removing the solvent is that factors which tend to favor formation of homogeneous particles often lead to particles having an undesirably low density, and vice versa. To form a substantially amorphous, homogeneous dispersion, it is desired to remove solvent rapidly. Since the spray solution is a homogeneous mixture of drug, polymer and solvent, the solvent should be removed on a time frame that is short relative to the time required for the drug and polymer to separate from each other. On the other hand, to form dense particles, solvent should be removed slowly. However, this may yield particles that are non-homogeneous and/or have undesirably high residual solvent levels.

Generally, the solvent evaporates sufficiently rapidly such that the droplets are essentially solid when they reach the outlet of the drying chamber and have a residual solvent content of less than 10 wt %. The large surface-to-volume ratio of the droplets and the large driving force for evaporation of solvent leads to actual drying times of a few seconds or less, and more typically less than 0.1 second. Drying times to a residual solvent level of less than 10 wt % should be less than 100 seconds, preferably less than 20 seconds, and more preferably less than 1 second.

In addition, the final solvent content of the solid dispersion as it exits the drying chamber should be low, since the residual solvent in the dispersion depresses the $T_g$ of the dispersion. Thus, drying conditions must be chosen to result in residual solvent levels that are low so that the glass transition temperature of the dispersion as it exits the drying chamber is high. Generally, the solvent content of the solid amorphous dispersion as it leaves the drying chamber should be less than about 10 wt %, preferably less than about 5 wt %, and more preferably less than about 3 wt %. Preferably, the residual solvent level is low enough so that the $T_g$ of the solid amorphous dispersion is at least the temperature of the exhaust drying gas at the outlet ($T_{OUT}$) less 20° C., and more preferably is at least $T_{OUT}$. For example, if the drying gas at the outlet has a temperature of 40° C., then the $T_g$ of the solid amorphous dispersion at the residual solvent level as it exits the drying chamber is preferably at least 20° C., and more preferably at least 40° C.

This highlights another potential challenge. In general, low residual solvent levels are conventionally achieved by raising the temperature of the drying gas $T_{IN}$, which in turn leads to a higher value of $T_{OUT}$. The inventors have circumvented this problem by using a relatively large flow rate of drying gas (relative to the flow rate of spray solution) at a relatively low inlet temperature $T_{IN}$. This leads to the desired result of achieving a relatively low $T_{OUT}$ while still achieving a low residual solvent level. This set of operating conditions generally leads to the desired goal of keeping $T_{OUT}$-$T_g$ less than 20° C., and preferably less than 0° C. In practice, the drying gas flow rate is fixed within a relatively narrow range as described above. Thus, the ratio of the drying gas flow rate to the spray solution flow rate is kept large for a given apparatus by lowering the spray solution flow rate (as well as $T_{IN}$ to keep $T_{OUT}$ low). This is in contrast to the conventional method of spray drying, as this lowers the productivity of the apparatus (kg product/hour).

Since the spray solution may consist of up to 80 wt % or more of solvent, substantial quantities of solvent must be removed during the evaporation process. The strong driving force for solvent evaporation is generally provided by maintaining the partial pressure of solvent in the drying chamber well below the vapor pressure of the solvent at the temperature of the drying droplets. This is accomplished by either (1) maintaining the pressure in the drying chamber at a partial vacuum (e.g., 0.01 to 0.50 bar); (2) mixing the liquid droplets of spray solution with a warm drying gas; or (3) both. In addition, a portion of the heat required for evaporation of solvent may also be provided by heating the spray solution.

Several parameters affect the rate and extent of solvent evaporation from the spray droplets and the characteristics of the resulting solid amorphous dispersion particles: (1) the pressure in the drying chamber; (2) the feed rate of the drying gas; (3) the composition of the drying gas; (4) the temperature of the spray solution; (5) the temperature of the drying gas at the inlet ($T_{In}$); (6) the feed rate of the spray solution; and (7) the droplet size of the atomized spray solution.

The pressure in the drying chamber and the feed rate of the drying gas are typically determined, within a relatively narrow operating range, by the particular configuration of the drying chamber and associated product collectors (such as cyclones, baghouses, etc.). The pressure within the spray dryer is typically maintained at a positive pressure relative to ambient pressure (e.g., greater than 1 bar). For example, for a NIRO (Niro A/S, Copenhagen; Denmark) PSD-2 spray dryer the pressure in the chamber may range from 1.017 to 1.033 bar, preferably 1.022 to 1.032 bar. The requirement for maintaining a positive pressure in the chamber is partly due to safety considerations, since this reduces the likelihood of air entering the drying chamber, and therefore minimizes exposure of the evaporated solvent to oxygen. In addition, the product collectors such as the cyclone typically operate more efficiently at positive pressures.

The drying gas entering the spray chamber should be at sufficiently high flow rate so as to be a sink for the evaporated solvent introduced into the chamber as the spray solution solvent. This provides a sufficiently dry environment to allow evaporation to occur under cool conditions. In order to achieve low residual solvent levels, the dewpoint of the solvent in the drying gas in the drying chamber must be low. The amount of solvent vapor in the drying gas (which determines the dewpoint) should be less than the amount of solvent vapor in equilibrium with the solid amorphous dispersion having the desired residual solvent content. For example, if it is desired that the solid amorphous dispersion exiting the drying chamber should have a residual solvent content of 10 wt % or less, the maximum amount of solvent vapor in the drying gas in the drying chamber should be less than the amount of solvent vapor that is present in a gas in equilibrium with a solid amorphous dispersion having 10 wt % residual solvent at a temperature of $T_{OUT}$. The maximum amount of solvent vapor that may be in the drying chamber may be calculated or determined experimentally for any given desired residual solvent level. If determined experimentally, a solid amorphous dispersion may be placed in a sealed container with dry gas. Solvent vapor may be added. The solid amorphous dispersion may be periodically evaluated to determine residual solvent content in equilibrium with the solvent vapor.

In practice, the need for a dry drying gas leads to very low dewpoints of the solvent in the drying gas. The dewpoint of the solvent in the drying chamber (if all of the solvent evaporated) should be substantially lower than $T_{OUT}$, and may be at least 10° C., at least 20° C., or even at least 30° C. less than $T_{OUT}$. For example, when spray drying with the solvent acetone at an outlet temperature $T_{OUT}$ of 40° C., the drying gas flow rate may be set so that the dewpoint of acetone in the drying chamber ranges from −5 to 5° C. This dry drying gas provides a strong driving force for rapid evaporation even under relatively cool conditions. For spray solution feed rates of 50 kg/hr to about 80 kg/hr, the feed rates of the drying gas may range from about 400 to about 600 m³/hr. For large feed rates of spray solution (e.g., feed rates of about 400 to 500 kg/hr), the drying gas feed rate may range from about 2000 to about 2500 m³/hr. This leads to relatively high ratios of drying gas flow rate to spray solution feed rate. Preferably, the ratio is at least 4 m³/kg, more preferably at least 4.5 m³/kg.

The drying gas may be virtually any gas, but to minimize the risk of fire or explosions due to ignition of flammable vapors, and to minimize undesirable oxidation of the drug, concentration-enhancing polymer, or other materials in the dispersion, an inert gas such as nitrogen, nitrogen-enriched air, or argon is utilized. In addition, the drying gas entering the drying chamber at the inlet may contain small amounts of the solvent in vapor form. Referring again to FIG. 1, the spray drying apparatus may include a drying gas recirculation system 46 that further comprises a solvent recovery system 48. As discussed in more detail below in connection with the drying gas recirculation system 48, the amount of solvent vapor in the drying gas affects the rate of evaporation of solvent from the droplets, and thus the density of the particles.

The temperature of the spray solution is typically determined by the solubility characteristics and stability of the constituents of the spray solution. In general, the spray solution may be held at a temperature ranging from about 0° C. to 50° C., and is usually maintained near room temperature. The temperature may be raised to improve the solubility of the drug or polymer in the solution. In addition, the temperature of the spray solution may be set at an elevated temperature to provide additional heat to the drying process so as to further increase the rate of evaporation of solvent from the droplets. The temperature may also be lowered if needed to improve the stability of the drug in the spray solution.

The temperature of the drying gas at the inlet to the chamber, referred to as $T_{IN}$, is set so as to drive evaporation of the solvent from the spray solution droplets but at the same time is controlled to maintain a relatively cool environment in the drying chamber. The drying gas is usually heated to provide energy to evaporate the incoming solvent to the drying chamber. In general, the drying gas may be heated to a temperature $T_{IN}$ greater than the boiling point of the solvent, and may range from about 5 to about 150° C. above the solvent boiling point. For example, when spray drying using the solvent acetone, which has a boiling point at ambient conditions of 56° C., a typical temperature range for $T_{IN}$ is from 60 to 200° C., when the drying chamber is operated at a pressure of about 1.035 BAR. In practice, the temperature of the drying gas entering the dryer inlet, $T_{IN}$, may be greater than 80° C., may be greater than 90° C., and may be greater than 100° C.

One set of constraints on the maximum value for $T_{IN}$ is the thermal properties of the spray dried solid amorphous dispersion. $T_{IN}$ should be low enough so as not to degrade the solid amorphous dispersion particles which are in the vicinity of the inlet for the drying gas. In general, $T_{IN}$ is maintained at less than the melting point of the solid amorphous dispersion. The preferred maximum value for $T_{IN}$ may be determined by heating the solid amorphous dispersion and determining the temperature at which the solid amorphous dispersion begins to degrade, for example by becoming discolored or by becoming sticky or tacky. $T_{IN}$ is preferably maintained below the temperature at which either of these conditions occur. Typically, $T_{IN}$ is less than 200° C., and preferably less than 150° C. In one embodiment, $T_{IN}$ ranges from 90 to 150° C., preferably from 100 to 130° C.

The feed rate of the spray solution will depend on a variety of factors, such as the drying gas inlet temperature $T_{IN}$, drying gas flow rate, the size of the drying chamber and atomizer. In practice, the feed rate of the spray solution when spray drying using a Niro PSD-2 spray dryer may range from 10 to 85 kg/hr, more preferably from 50 to 75 kg/hr. The invention has particular utility as the feed rate of the spray solution increases, allowing production of increasing quantities of product. In preferred embodiments, the feed rate of the spray solution is at least 50 kg/hr, preferably at least 100 kg/hr, more preferably at least 200 kg/hr, and even more preferably at least 400 kg/hr. In one embodiment, the spray solution feed rate may range from 400 kg/hr to 600 kg/hr.

The feed rate of the spray solution is controlled, in conjunction with $T_{IN}$, so as to achieve efficient spray drying, high product yield, and good particle characteristics. The acceptable ranges for the feed rate of the spray solution and $T_{IN}$ may be determined by the thermodynamics of the drying process, which are easily quantified. The heat content and flow rate of the heated drying gas are known; the heat content, heat of vaporization, and flow rate of the spray solution are known; and the heat loss from the drying chamber to its environment is quantifiable. Therefore, the energy and mass balances of the inlet streams (spray solution and drying gas) allow prediction of the outlet conditions for the process: namely, the outlet temperature of the drying gas exiting the drying chamber (referred to as $T_{OUT}$) and the solvent vapor concentration in the drying gas in the drying chamber.

Figure 3:
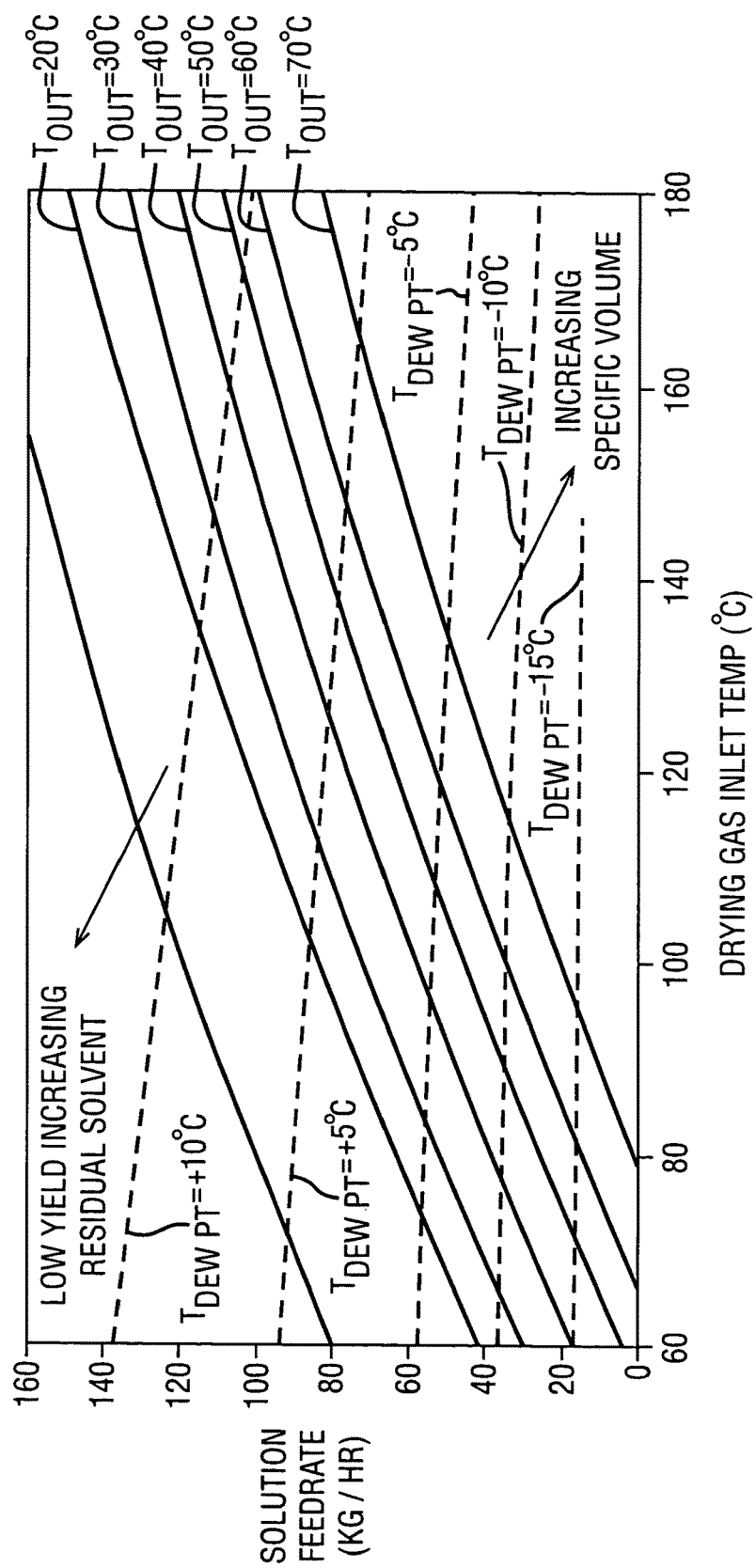
FIG. 3 is an isotherm chart for an exemplary set of spray drying conditions.

The mass and energy balances for a given drying chamber, spray solution, and set of operating parameters can be shown on an isotherm chart (similar to a psychrometric chart). FIG. 3 is an exemplary isotherm chart for a Niro PSD-2 pilot-scale spray-dryer. This chart is for a spray solution comprising 16 wt % solids and 84 wt % acetone and a drying gas flow rate of 530 m³/hr. The horizontal axis shows inlet temperature of the drying gas $T_{IN}$ from 60° C. to a maximum of 180° C. The vertical axis shows the feed rate of the spray solution in kg/hr. The diagonal solid lines show constant drying gas outlet temperature $T_{OUT}$. The dashed diagonal lines show constant dewpoint $T_{dewpt}$ of the solvent in the drying gas. Charts of this type can be used to determine potential throughputs of a given drying chamber for a given spray solution. Furthermore, the isotherm charts can be used to identify ranges of operating conditions where solid amorphous dispersions having the desired qualities will be manufactured.

Turning now to FIG. 3 in more detail, the relationship of various process conditions to the resulting solid amorphous dispersions may be observed. One limit on the spray drying process is the relationship between the dew point of the solvent vapor in the drying gas and $T_{OUT}$. Once the dew point of the solvent vapor in the drying gas exceeds $T_{OUT}$, the drying gas in the drying chamber is saturated in solvent vapor and full drying of the solid amorphous dispersions is not possible. In fact, even approaching this limit leads to significant amounts of the spray solution striking the walls of the drying chamber due to insufficient drying time and/or distance. This region is labeled as the "Low Yield-Increasing Residual Solvent" area in the chart. Thus, the spray conditions should be chosen so as to maintain the dew point substantially below $T_{OUT}$. Preferably, the dew point is at least 20 to 30° C. less than $T_{OUT}$.

Another limit on the spray drying process is the relationship between $T_{OUT}$ and both the melt and the glass transition temperature of the resulting solid amorphous dispersion particles. If $T_{OUT}$ is greater than the melt temperature, then the solid amorphous dispersion particles may melt on contact with the drying chamber walls, resulting in poor yield. In addition, it is also preferred to maintain $T_{OUT}$ below the glass transition temperature of the solid amorphous dispersion. As described above, mobility of the drug in the solid amorphous dispersion is a function of the glass transition temperature of the solid amorphous dispersion. When the temperature of the solid amorphous dispersion is below its glass transition temperature, the mobility of the drug is low, and the drug remains homogeneously dispersed in the amorphous state throughout the polymer. However, if the solid amorphous dispersion is exposed to temperatures greater than its glass transition temperature for sustained periods of time, the mobility of the drug is high during that period of time, and the drug may phase separate in the dispersion, and may ultimately crystallize. Thus, substantially homogeneous, substantially amorphous dispersions are most likely to result when $T_{OUT}$ is maintained below the glass transition temperature of the solid amorphous dispersion. Turning to FIG. 3, the glass transition temperature of the solid amorphous dispersion is about 30° C. Thus, the region below the diagonal line representing $T_{OUT}$ of 50° C. is more likely to lead to non-homogeneous product. Preferably, $T_{OUT}$ is less than the $T_g$ of the solid amorphous dispersion particle plus 20° C. ($T_g$+20° C.), and preferably less than the $T_g$.

In addition, the inventors have found that for solid amorphous dispersions comprising at least about 50 wt % polymer, $T_{OUT}$ generally indicates the density of and residual solvent in the solid amorphous dispersions. The inventors have found that as $T_{OUT}$ increases, the density of the particles decreases. Without wishing to be bound by any particular theory, the inventors believe that at high drying temperatures, the droplets quickly form a dry, external "skin." This skin establishes the surface area of the particle. When the temperature within the droplet is high, the droplet dries in the shape of a hollow sphere, resulting in low density. At lower temperatures, the droplets do not form a dry skin as quickly, and the skin when it does form collapses during evaporation into denser particles. Lowering the temperature within the drying chamber, as reflected by a lower $T_{OUT}$, results in slower drying and a higher density product. However, if $T_{OUT}$ is too low, then the residual solvent level in the solid amorphous dispersion will be too high. Referring again to FIG. 3, the area above $T_{OUT}$ greater than 10° C. is labeled as "Low Yield" due to increasing residual solvent in the solid amorphous dispersion. In general, it is desired to maintain $T_{OUT}$ above the solvent dewpoint and below the solvent boiling point, and preferably from about 5 to about 25° C. below the solvent boiling point, and more preferably from about 10 to about 20° C. below the solvent boiling point.

In practice, the feed rate of the drying gas, pressure in the chamber, and heat of the spray solution are typically predetermined within narrow ranges. Accordingly, the feed rate of the spray solution and the temperature of the drying gas $T_{IN}$ are controlled so as to obtain a satisfactory $T_{OUT}$ as described above. Returning now to FIG. 3, the optimal region of operation for the dryer represented by FIG. 3 is the diagonal band between the $T_{OUT}$ isotherm lines of 50° C. and 30° C. Thus, $T_{IN}$ and the feed rate of the spray solution are controlled so as to achieve a $T_{OUT}$ within this band. To maximize the thermal capacity of the drying chamber, the conditions would be chosen to operate at a high inlet temperature $T_{IN}$ and high spray solution feed rate corner of the band. However, density of the particles often increases as the ratio of drying gas to spray solution feed rate increases. Thus it may be preferred to operate at the lower left corner of the band for a given $T_{OUT}$ (that is, lower spray solution feed rates and lower $T_{IN}$), even though this does not result in optimal throughput of the feed solution through the drying chamber. This leads to lower $T_{dewpt}$, and thus a dryer drying gas. In FIG. 3, operating in a regime where $T_{dewpt}$ is from −5 to 5° C. yields homogeneous solid amorphous dispersions that are dense (<10 cc/g specific volume) and have low residual solvent (<10 wt %). In addition, as discussed above,

2. Spray Drying Equipment
a. Atomizer

The spray solution is fed into the drying chamber through the atomizer to form small droplets. Forming small droplets results in a high ratio of surface area to volume, thus aiding evaporation of solvent. In general, to achieve rapid evaporation of the solvent, it is preferred that the size of droplets formed during the spray-drying process are less than about 500 μm in diameter, and preferably less than about 300 μm. Droplet sizes generally range from 1 μm to 500 μm in diameter, with 5 to 200 μm being more typical. Exemplary atomizers include pressure nozzles, rotary atomizers, and two-fluid nozzles. When selecting an atomizer for use in forming a homogeneous solid amorphous dispersion, several factors should be considered, including the desired feed rate of the spray solution, the maximum allowable liquid pressure, and the viscosity and surface tension of the spray solution. The relationship between these factors and their influence on droplet size and droplet size distribution are well known in the art.

$T_{IN}$ may also be moderated if it reduces accumulation of solid amorphous dispersion in the drying chamber due to localized melting, charring or burning of spray-dried product on any excessively hot surfaces in the drying chamber.

In a preferred embodiment, the atomizer is a pressure nozzle. By "pressure nozzle" is meant an atomizer that produces droplets with an average droplet diameter of 10 μm or larger, with less than about 10 vol % of the droplets having a size less than about 1 μm. Generally, an appropriately sized and designed pressure nozzle is one that will produce droplets within a 10 to 100 μm range when the spray solution is pumped through the nozzle at the desired rate. Thus, for example, when it is desired to deliver 400 g/min of a spray solution to a PSD-1 dryer, a nozzle must be chosen that is matched to the viscosity and flow rate of the solution to achieve the desired average droplet size. Too large a nozzle will deliver too large a droplet size when operated at the desired flow rate. This is particularly true at higher spray solution viscosity, since the solution viscosity directly affects the performance of the atomizer. As the viscosity increases, the droplet size increases and the nozzle pressure decreases for a constant flow rate of spray solution. Droplets that are too large result in the rate of drying being too slow, which can yield nonhomogeneous dispersions or, if still fluid when they reach the spray-dryer wall, the droplets may stick to or even coat the dryer wall, resulting in low or no yield of the desired product. In such cases, the height of the spray-drying chamber can be increased to provide an increased minimum distance that a droplet travels before impinging on the walls of the drying chamber or collection cone. Such a modified spray-drying apparatus allows for use of atomizing means that produce larger droplets. Details of such a modified spray-drying apparatus are described below. Use of too small a nozzle can yield droplets that are undesirably small or may require an unacceptably high pump pressure to achieve the desired flow rate, particularly for high viscosity feed solutions.

Figure 4:
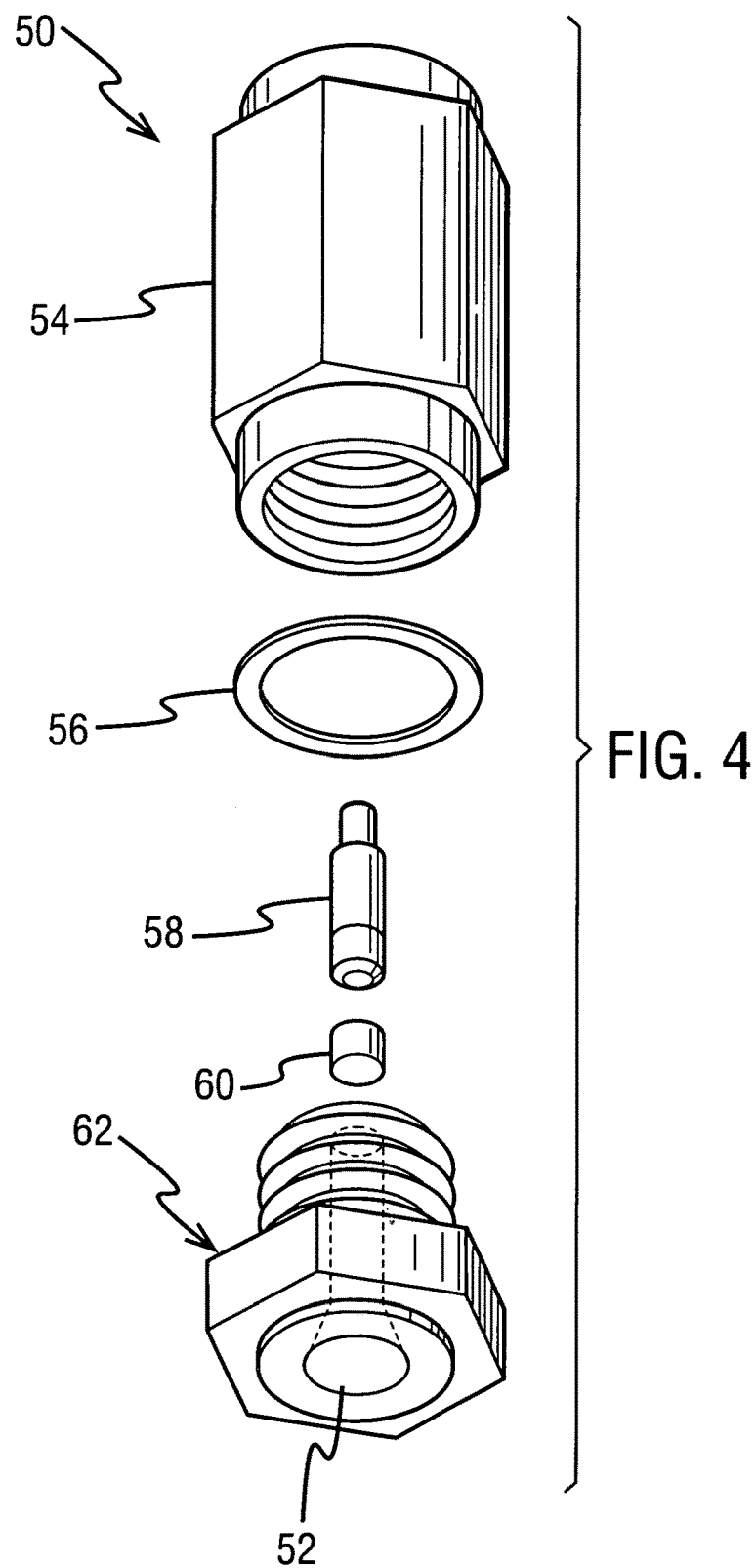
FIG. 4 is an assembly view of a pressure nozzle.

A particularly preferred type of pressure nozzle is one with an exit orifice in the shape of a cone. Such a pressure nozzle is shown in assembly view in FIG. 4. The pressure nozzle 50 has an inlet orifice located at the top (not shown) for receiving the spray solution feed and an exit orifice at the bottom 52 for spraying the liquid droplets into the spray chamber 28. FIG. 4 shows a pressure swirl nozzle comprising a housing 54, a gasket 56, a swirl chamber 58, an orifice insert 60, and a nozzle body 62. FIG. 5 shows a cross-section of an exemplary nozzle body 62. The internal tapered walls 64 of the nozzle body 62 adjacent to the exit orifice 52 define a cone shape that corresponds with the cone angle of the sprayed droplets. Such a cone shape has the advantage of reducing build-up of dried solid material on the outer face of the nozzle 66 adjacent to the exit orifice 52. An exemplary pressure nozzle having internal walls defining such a cone shape is the DELAVAN SDX Cone Face nozzle (Delavan, Inc.; Bamberg, S.C.). The pressure nozzle may be a swirl pressure nozzle, as is well known in the art. Such pressure nozzles, such as is shown in FIGS. 4 and 5, include a swirl chamber which produces a hollow "cone" of the spray solution in the form of a solution film or sheet, which breaks apart into a hollow cone-shaped droplet cloud.

The vast majority of atomizers atomize the spray solution into droplets with a distribution of sizes. The size distribution of droplets produced by an atomizer can be measured by several techniques, including mechanical techniques, such as the molten-wax and frozen-drop techniques; electrical techniques, such as charged-wire and hot-wire techniques; and optical techniques, such as photography and light-scattering techniques. Exemplary devices for determining the droplet size distribution produced by an atomizer include a Malvern Particle Size Analyzer, available from Malvern Instruments Ltd. of Framingham, Mass., and a Doppler Particle Analyzer available from TSI, Inc.; Shoreview, Minn. Further details about the principles used to determine droplet size and droplet size distribution using such instruments can be found in Lefebvre, *Atomization and Sprays* (1989).

The data obtained using a droplet size analyzer can be used to determine several characteristic diameters of the droplets. One of these is $D_{10}$, the diameter corresponding to the diameter of droplets that make up 10% of the total liquid volume containing droplets of equal or smaller diameter. In other words, if $D_{10}$ is equal to 1 μm, 10 vol % of the droplets have a diameter less than or equal to 1 μm. Thus, it is preferred that the atomizing means produce droplets such that $D_{10}$ is greater than about 1 μm, meaning that 90 vol % of the droplets have a diameter of greater than 1 μm. This requirement ensures the number of fines in the solidified product (i.e., particles with diameters of less than 1 μm) is minimized. Preferably, $D_{10}$ is greater than about 10 μm, more preferably greater than about 15 μm.

Another useful characteristic diameter of the droplets produced by an atomizing means is $D_{90}$, the diameter corresponding to the diameter of droplets that make up 90% of the total liquid volume containing droplets of equal or smaller diameter. In other words, if $D_{90}$ is equal to 100 μm, 90 vol % of the droplets have a diameter less than or equal to 100 μm. For producing substantially homogeneous, substantially amorphous dispersions using the technology of the present invention, $D_{90}$ should preferably be less than about 300 μm, more preferably less than 250 μm. If $D_{90}$ is too high, the rate of drying of the larger droplets may be too slow, which can yield nonhomogeneous dispersions or, if still fluid when they reach the spray dryer wall, the larger droplets may stick to or coat the dryer wall, as noted above.

Another useful parameter is "Span," defined as $$\text{Span} = \frac{D_{90} - D_{10}}{D_{50}},$$

where $D_{50}$ is the diameter corresponding to the diameter of drops that make up 50% of the total liquid volume containing drops of equal of smaller diameter, and $D_{90}$ and $D_{10}$ are defined as above. Span, sometimes referred to in the art as the Relative Span Factor or RSF, is a dimensionless parameter indicative of the uniformity of the drop size distribution. Generally, the lower the Span, the more narrow the droplet size distribution produced by the atomizing means, which in turn generally leads to a narrower particle size distribution for the dried particles, resulting in improved flow characteristics. Preferably, the Span of the droplets produced by the atomizer is less than about 3, more preferably less than about 2, and most preferably less than about 1.5.

The size of the solid amorphous dispersion particles formed in the drying chamber are generally somewhat smaller than the size of the droplets produced by the atomizer. Typically, the characteristic diameter of the solid amorphous dispersion particles is about 80% of the characteristic diameter of the droplets. Since it is desired to avoid small amorphous dispersion particles due to poor flow characteristics, the nozzle is typically selected to produce the largest droplet sizes that may be sufficiently dried in the spray drying apparatus.

As indicated above, the selection of the atomizer will depend upon the scale of the spray-drying apparatus used. For smaller scale apparatus such as the Niro PSD-1 that can spray about 5-400 g/min of a solvent-bearing feed, examples of suitable atomizers include the SK and TX spray dry nozzle series from Spraying Systems of Wheaton, Ill.; the WG series from Delavan LTV of Widnes, Cheshire, England; and the Model 121 nozzle from Dusen Schlick GmbH of Untersiemau, Germany. For a larger scale apparatus that can spray about 25-600 kg/hr of a solvent-bearing feed, exemplary atomizers include those listed above, as well as the SDX and SDX III nozzles from Delavan LTV, and the Spraying Systems SB series.

In many cases, the spray solution is delivered to the atomizer under pressure. The pressure required is determined by the design of the atomizer, the size of the nozzle orifice, the viscosity and other characteristics of the solvent-bearing feed, and the desired droplet size, and size distribution. Generally, feed pressures should range from 1 to 500 BAR or more, with 2 to 100 BAR being more typical. For a PSD-2 spray dryer using a pressure nozzle as the atomizer, the nozzle pressure may be from 40 to 55 BAR at feed flow rates of from 50 to about 90 kg/hr. For a PSD-5 spray dryer using a pressure nozzle as the atomizer, the nozzle pressure may be from 140 to 210 BAR at spray solution feed rates of from about 400 to about 500 kg/hr.

When using a pressure nozzle, the pump which directs the spray solution to the atomizer should be capable of generating sufficient pressure at the desired feed rate with low pulsing. Exemplary pumps include positive displacement diaphragm pump, and piston pumps. Referring again to FIG. 1, pump 26 may be a positive displacement diaphragm pump, model VED available from Bran+Leubbe GmbH; Norderstedt, Germany.

b. Gas Disperser

The spray drying apparatus also includes a gas disperser to mix the drying gas with the droplets. A gas disperser is designed so that the newly introduced drying gas mixes adequately with the atomized spray droplets so that evaporation occurs in such a manner that all the droplets are dried sufficiently quickly to minimize product buildup in the spray chamber and on the atomizer. Therefore gas dispersers are designed with the atomizer spray pattern, drying gas flow rate and the drying chamber dimensions in mind.

FIG. 1 shows schematically gas disperser 32. FIG. 6 shows a cross-sectional schematic of a drying chamber 100, which includes a gas-dispersing means 102 situated within drying chamber 100 and below drying chamber top 104. Drying gas enters the chamber 108 and passes through openings 110 in the plate 112. Gas-dispersing means 102 allows drying gas to be introduced into chamber 100 so that it is initially generally parallel to the axis of atomizing means 106 and is distributed relatively evenly across the diameter of the apparatus, shown schematically by the multiple downwardly pointing arrows in the upper portion of FIG. 6. Details of this gas disperser are described more fully in commonly assigned U.S. provisional patent application 60/354,080, filed Feb. 2, 2002, (PC23195) herein incorporated by reference. Alternatively, a DPH gas disperser available from Niro, Inc. Columbia, Md. may be used.

c. Drying Chamber

Figure 7:
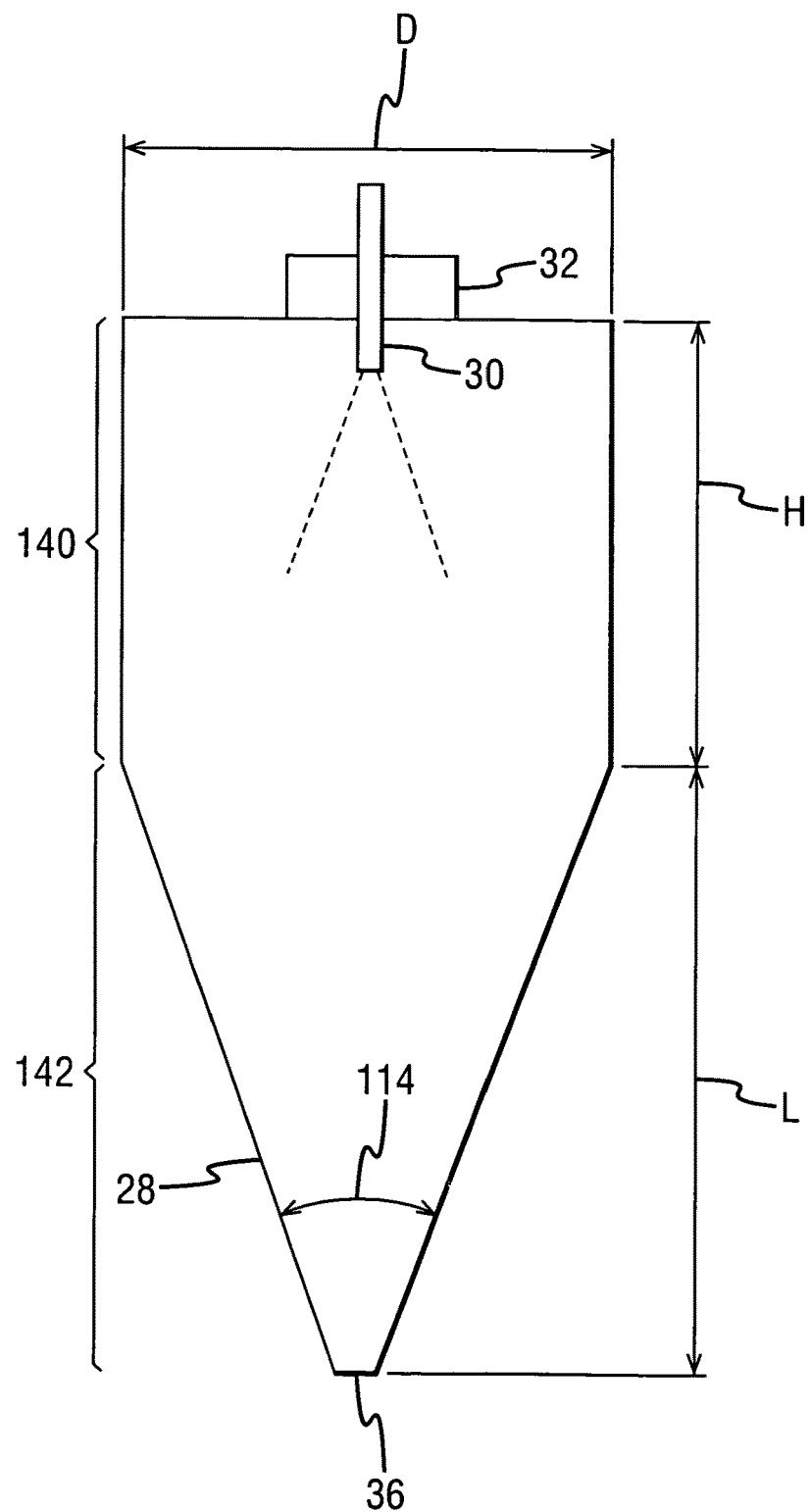
FIG. 7 is a schematic view in cross section of an exemplary drying chamber.

The size and shape of the drying chamber is designed to allow sufficient evaporation of the spray solution droplets prior to striking any surface of the chamber, and to allow efficient product collection. Referring to FIG. 7, typically the drying chamber has an upper cylindrical portion 140 and a lower collection cone 142. The distance between the atomizer and the internal surfaces of the drying chamber generally limits the size of droplets that can be evaporated and, in turn, the amount of product particles that may be formed without excessive build-up of material on the side walls of the drying chamber and collection cone.

The height H of the upper cylindrical portion 140 of the drying chamber should be tall enough to allow the atomized droplets sufficient time to evaporate before striking the lower portion of the drying chamber. The height H of the upper portion of the drying chamber that provides a sufficient minimum distance the droplets travel before impinging on the walls of drying chamber or of collection cone is a function of several factors, including (1) the drying characteristics of the solvent-bearing feed, (2) the flow rates of solvent-bearing feed and drying gas to the spray-dryer, (3) the inlet temperature of the drying gas, (4) the droplet size and droplet size distribution (5) the average residence time of material in the spray-dryer (6) the gas circulation pattern in the drying chamber, and (7) the atomization pattern. For drying gas flows of 500 $m^3$/hr, a height H in excess of about 1 m is generally preferred. The height will depend in part on the particular gas disperser chosen. For the gas disperser shown in FIG. 6, a taller height H is desired, as described more fully in commonly assigned U.S. provisional patent application Ser. No. 60/354,080.

While the height of the drying chamber is critical to determine the minimum distance a droplet travels before impinging on a surface of the drying chamber, the volume of the drying chamber is also important. The capacity of a spray-dryer is determined, in part, by matching the feed rate of the spray solution to the temperature and flow rate of the drying gas. As described above, the temperature and flow rate of the drying gas must be sufficiently high so that sufficient heat for evaporating the spray solution is delivered to the spray-drying apparatus. Thus, as the feed rate of the spray solution is increased, the flow rate and/or temperature of the drying gas must be increased to provide sufficient energy for formation of the desired product. Since the allowable temperature of the drying gas is often limited by the chemical stability of the drug present in the spray solution, the drying gas flow rate is often increased to allow for an increased capacity (i.e., increased feed rate of the spray solution) of the spray-drying apparatus. For a drying chamber with a given volume, an increase in the drying gas flow rate will result in a decrease in the average residence time of droplets or particles in the dryer, which could lead to insufficient time for evaporation of solvent from the droplets to form a solid particle prior to impinging on a surface in the drying chamber, even though the drying chamber has a greater height than a conventional dryer. As a result, the volume of the dryer must be sufficiently large so that the droplet is sufficiently dry by the time it impinges on internal surfaces of the drying chamber to prevent build-up of material.

One may take into account this drying time by the "average residence time" τ, defined as the ratio of the volume of the drying chamber to the volumetric flow rate of drying gas fed to the drying apparatus, or $$\tau = \frac{V_{dryer}}{G},$$

where $V_{dryer}$ is the volume of the drying chamber and G is the volumetric flow rate of drying gas fed to the drying chamber. The volume of the drying chamber is the sum of the volumes of the upper portion of the drying chamber 110 and collection cone 112. For a cylindrical spray-drying apparatus with a diameter D, a height H of the drying chamber, and a height L of the collection cone, the volume of the dryer $V_{dryer}$ is given as $$V_{dryer} = \frac{\pi}{4}D^2H + \frac{\pi}{12}D^2L$$

The inventors have determined that the average residence time should be at least 10 seconds to ensure that the droplets have sufficient time to dry prior to impinging on a surface within the spray-dryer; more preferably, the average residence time is at least 15 seconds and most preferably at least 20 seconds.

For example, for a volumetric flow of drying gas of 0.25 $m^3$/sec and an average residence time of 20 seconds, the required volume of the spray-drying apparatus can be calculated as follows:

$$V_{dryer} = \tau \cdot G = 20\ \text{sec} \cdot 0.25\ \text{m}^3/\text{sec} = 5\ \text{m}^3.$$

Thus, for a spray-dryer with a volume of 5 $m^3$, a height H of 2.3 m and a collection cone 112 with a cone angle 114 of 60° (meaning that the height L of the collection cone 112 is equal to the diameter D of the drying chamber, or L=D), the required diameter D of the spray-drying chamber can be calculated from the above equation, as follows:

$$V_{dryer} = \frac{\pi}{4}D^2H + \frac{\pi}{12}D^2L = \frac{\pi}{4}D^2H + \frac{\pi}{12}D^3 = 5 = \frac{\pi}{4}D^2 2.3 + \frac{\pi}{12}D^3,$$

$$\text{or } D = 1.5\ \text{m}.$$

Provided the diameter of the drying chamber is at least 1.5 m, the average residence time of particles in the dryer will be at least 20 seconds, and the droplets produced by the atomizer can be sufficiently dry by the time they impinge on the surface of the dryer to minimize build-up of material on the walls of the drying chamber and collection cone, given appropriate height and diameter, atomization pattern and gas flow pattern.

The aspect ratio of the drying chamber is the ratio of the Height H of the upper portion 140 of the drying chamber divided by the diameter D of the chamber. For example, if a drying chamber has a height H of 2.6 m and a diameter D of 1.2 m, then the drying chamber has an aspect ratio of 2.6/1.2=2.2. In general, the aspect ratio of the drying chamber may vary from about 0.9 to about 2.5. For the gas DPH gas disperser available from Niro, Inc., an aspect ratio of about 1 to 1.2 works well, while for the gas disperser shown in FIG. 6, a larger aspect ratio of about 2 or greater is desired. The cone angle 114 of the collection cone is selected so as to achieve efficient product collection. The cone angle 114 may vary from about 30° to about 70°, preferably 40° to about 60°.

In one embodiment, a drying chamber capable of spray solution feed rates of from 10 kg/hr to about 90 kg/hr has a height H of about 2.6 m, a diameter of about 1.2 m, an aspect ratio of 2.2, a cone angle of about 60° C., a cone height L of about 1.3 m, and a gas residence time of about 30 to 35 seconds at a gas flow rate of about 400 to about 550 $m^3$/hr. In another embodiment, a drying chamber capable of spray solution feed rates of from 400 kg/hr to about 500 kg/hr has a height H of about 2.7 m, a diameter D of about 2.6 m, an aspect ratio of about 1, a cone angle of about 40° C., a cone height L of about 3.7 m, and a gas residence time of about 30 to 35 seconds at a gas flow rate of about 2000 to about 2500 $m^3$/hr.

c. Collection of Solid Amorphous Dispersions

Referring now again to FIG. 1, the solid amorphous dispersion particles exit the spray drying chamber 28 and are transported with the exhaust drying gas to one or more product collectors. Exemplary product collectors include cyclones, bag houses, and dust collectors. For example, in the system shown in FIG. 1, a cyclone 38 collects the majority of the solid amorphous dispersion particles. The solid amorphous dispersion particles exit the cyclone 38 through a pair of valves 120 and 122, and are collected in a container 124 such as a drum. The cyclone 38 may include a vibrator (not shown) or other mechanical device to agitate the particles within the cyclone 38 as is known in the art to improve the efficiency of removal of material from the cyclone 38. The exhaust drying gas exits the cyclone 38 and passes through the baghouse 126, which collects small, fine particles that bypassed the cyclone 38.

d. Recirculation of Drying Gas

Since the spray drying process uses large volumes of drying gas, it is often desired to recirculate the drying gas. Referring again to FIG. 1, the spray drying system may optionally include a drying gas recirculation system 46, which forms a closed loop from the drying chamber outlet 36 to the drying chamber inlet 32 for recirculating the drying gas. The drying gas recirculation system includes a blower 128 following the baghouse 126 to direct the drying gas to a solvent recovery system 48. Exemplary solvent recovery systems include condensers, wet-gas scrubbers, semi-permeable membranes, absorption, biological gas scrubbers, adsorption, and trickle bed reactors. As shown in FIG. 1, the solvent recovery system is a condenser 130. The condenser 130 cools the drying gas to remove solvent. The drying gas then proceeds to a process heater 132 where the drying gas is heated to achieve the desired inlet temperature $T_{IN}$. Another blower 134 then directs the drying gas into the gas disperser 32, so that the drying gas may enter the drying chamber 28 through inlet 34. The recirculation loop 46 also includes an outlet 136 to allow the recirculated drying gas to be vented, and an inlet 138 to allow addition of drying gas to the recirculation loop.

In the solvent removal system 48, the condenser 130 is a shell and tube heat exchanger available from various sources, such as from Atlas Industrial Manufacturing (Clifton, N.J.). Typical condenser outlet temperatures range from about −30° to about 15° C., and will depend on the freezing point of the solvent. For example, when using acetone as the solvent, the condenser outlet temperature ranges from −30° to 0° C., preferably from −25° to −5° C. The condenser typically operates at an outlet temperature such that the condenser removes only a portion of the solvent vapor from the drying gas. For example, when using the solvent acetone, the condenser temperature may be set so that the drying gas exiting the condenser has an acetone relative vapor concentration of from about 5 to 50 wt %, more preferably from about 15 to 30 wt %. Alternatively, the dew point of acetone in the drying gas exiting the condenser may range from about −20° C. to about 25° C., more preferably from about −5° C. to about 20° C.

The inventors have found that retaining a small amount of residual solvent vapor in the drying gas can improve the physical properties of the resulting spray dried dispersions. This is a surprising result, since the conventional wisdom has held that the drying gas should be as dry as possible in order to achieve rapid evaporation of solvent. In particular, using a drying gas containing a small amount of solvent can decrease the residual solvent and specific volume of the solid amorphous dispersion particles exiting the drying chamber while still producing a homogeneous solid amorphous dispersion. Preferably, the amount of solvent vapor in the drying gas ranges from 5 to about 50 wt %.

Alternatively, since the amount of solvent vapor in the drying gas is a function of the efficiency of the solvent removal system, the solvent removal system may be operated so as to allow a small amount of solvent to exit the solvent removal system with the recirculated drying gas. For example, for the drying gas recirculation system shown in FIG. 1, the condenser may be operated at a temperature that allows a small amount of solvent vapor to pass through the condenser. A condenser outlet temperature of from about −5 to about 5° C. for an acetone based spray solution results in a sufficient amount of solvent vapor in the drying gas. However, care should be taken not to include too much solvent vapor in the drying gas, since at higher amounts of solvent vapor in the drying gas residual solvent in the solid amorphous dispersion begins to rise, corresponding to less efficient drying of the droplets, and ultimately no drying in the case where the drying gas becomes saturated with solvent vapor.

Without wishing to be bound by any theory, the inventors believe that the presence of small amounts of solvent vapor in the drying gas may improve drying by one or both of the following effects. First, the solvent vapor in the drying gas may cause the droplets of spray solution to dry more evenly by delaying the formation of a skin (as discussed above). Second, the solvent vapor, due to its greater heat capacity than the drying gas, may provide more heat energy into the drying chamber for a given temperature and flow of drying gas compared with the same flow of dry drying gas at the same temperature. In either case, adding a small amount of solvent vapor to the drying gas decreases residual solvent and decreases specific volume of the solid amorphous dispersion particles exiting the drying chamber.

The Drug

The term "drug" is conventional, denoting a compound having beneficial prophylactic and/or therapeutic properties when administered to an animal, especially humans. The drug does not need to be a low-solubility drug in order to benefit from this invention, although low-solubility drugs represent a preferred class for use with the invention. Even a drug that nonetheless exhibits appreciable solubility in the desired environment of use can benefit from the increased solubility/bioavailability made possible by this invention if it reduces the size of the dose needed for therapeutic efficacy or increases the rate of drug absorption in cases where a rapid onset of the drug's effectiveness is desired.

Preferably, the drug is a "low-solubility drug," meaning that the drug may be either "substantially water-insoluble," which means that the drug has a minimum aqueous solubility at physiologically relevant pH (e.g., pH 1-8) of less than 0.01 mg/mL, "sparingly water-soluble," that is, has an aqueous solubility up to about 1 to 2 mg/mL, or even low to moderate aqueous-solubility, having an aqueous-solubility from about 1 mg/mL to as high as about 20 to 40 mg/mL. The invention finds greater utility as the solubility of the drug decreases. Thus, compositions of the present invention are preferred for low-solubility drugs having a solubility of less than 10 mg/mL, more preferred for low-solubility drugs having a solubility of less than 1 mg/mL, and even more preferred for low-solubility drugs having a solubility of less than 0.1 mg/mL. In general, it may be said that the drug has a dose-to-aqueous solubility ratio greater than 10 mL, and more typically greater than 100 mL, where the drug solubility (mg/mL) is the minimum value observed in any physiologically relevant aqueous solution (e.g., those with pH values between 1 and 8) including USP simulated gastric and intestinal buffers, and dose is in mg. Thus, a dose-to-aqueous solubility ratio may be calculated by dividing the dose (in mg) by the solubility (in mg/mL).

Preferred classes of drugs include, but are not limited to, antihypertensives, antianxiety agents, anticlotting agents, anticonvulsants, blood glucose-lowering agents, decongestants, antihistamines, antitussives, antineoplastics, beta blockers, anti-inflammatories, antipsychotic agents, cognitive enhancers, cholesterol-reducing agents, anti-atherosclerotic agents, antiobesity agents, autoimmune disorder agents, anti-impotence agents, antibacterial and antifungal agents, hypnotic agents, anti-Parkinsonism agents, anti-Alzheimer's disease agents, antibiotics, anti-depressants, antiviral agents, glycogen phosphorylase inhibitors, and cholesteryl ester transfer protein inhibitors.

Each named drug should be understood to include any pharmaceutically acceptable forms of the drug. By "pharmaceutically acceptable forms" is meant any pharmaceutically acceptable derivative or variation, including stereoisomers, stereoisomer mixtures, enantiomers, solvates, hydrates, isomorphs, polymorphs, pseudomorphs, neutral forms, salt forms and prodrugs. Specific examples of antihypertensives include prazosin, nifedipine, amlodipine besylate, trimazosin and doxazosin; specific examples of a blood glucose-lowering agent are glipizide and chlorpropamide; a specific example of an anti-impotence agent is sildenafil and sildenafil citrate; specific examples of antineoplastics include chlorambucil, lomustine and echinomycin; a specific example of an imidazole-type antineoplastic is tubulazole; a specific example of an anti-hypercholesterolemic is atorvastatin calcium; specific examples of anxiolytics include hydroxyzine hydrochloride and doxepin hydrochloride; specific examples of anti-inflammatory agents include betamethasone, prednisolone, aspirin, piroxicam, valdecoxib, carprofen, celecoxib, flurbiprofen and (+)-N-{4-[3-(4-fluorophenoxy)phenoxy]-2-cyclopenten-1-yl}-N-hyroxyurea; a specific example of a barbiturate is phenobarbital; specific examples of antivirals include acyclovir, nelfinavir, and virazole; specific examples of vitamins/nutritional agents include retinol and vitamin E; specific examples of beta blockers include timolol and nadolol; a specific example of an emetic is apomorphine; specific examples of a diuretic include chlorthalidone and spironolactone; a specific example of an anticoagulant is dicumarol; specific examples of cardiotonics include digoxin and digitoxin; specific examples of androgens include 17-methyltestosterone and testosterone; a specific example of a mineral corticoid is desoxycorticosterone; a specific example of a steroidal hypnotic/anesthetic is alfaxalone; specific examples of anabolic agents include fluoxymesterone and methanstenolone; specific examples of antidepression agents include sulpiride, [3,6-dimethyl-2-(2,4,6-trimethyl-phenoxy)-pyridin-4-yl]-(1-ethylpropyl)-amine, 3,5-dimethyl-4-(3'-pentoxy)-2-(2',4',6'-trimethylphenoxy)pyridine, pyroxidine, fluoxetine, paroxetine, venlafaxine and sertraline; specific examples of antibiotics include carbenicillin indanylsodium, bacampicillin hydrochloride, troleandomycin, doxycyline hyclate, ampicillin and penicillin G; specific examples of anti-infectives include benzalkonium chloride and chlorhexidine; specific examples of coronary vasodilators include nitroglycerin and mioflazine; a specific example of a hypnotic is etomidate; specific examples of carbonic anhydrase inhibitors include acetazolamide and chlorzolamide; specific examples of antifungals include econazole, terconazole, fluconazole, voriconazole, and griseofulvin; a specific example of an antiprotozoal is metronidazole; specific examples of anthelmintic agents include thiabendazole and oxfendazole and morantel; specific examples of antihistamines include astemizole, levocabastine, cetirizine, decarboethoxyloratadine and cinnarizine; specific examples of antipsychotics include ziprasidone, olanzepine, thiothixene hydrochloride, fluspirilene, risperidone and penfluridole; specific examples of gastrointestinal agents include loperamide and cisapride; specific examples of serotonin antagonists include ketanserin and mianserin; a specific example of an anesthetic is lidocaine; a specific example of a hypoglycemic agent is acetohexamide; a specific example of an anti-emetic is dimenhydrinate; a specific example of an antibacterial is cotrimoxazole; a specific example of a dopaminergic agent is L-DOPA; specific examples of anti-Alzheimer's Disease agents are THA and donepezil; a specific example of an anti-ulcer agent/H2 antagonist is famotidine; specific examples of sedative/hypnotic agents include chlordiazepoxide and triazolam; a specific example of a vasodilator is alprostadil; a specific example of a platelet inhibitor is prostacyclin; specific examples of ACE inhibitor/antihypertensive agents include enalaprilic acid and lisinopril; specific examples of tetracycline antibiotics include oxytetracycline and minocycline; specific examples of macrolide antibiotics include erythromycin, clarithromycin, and spiramycin; a specific example of an azalide antibiotic is azithromycin; specific examples of glycogen phosphorylase inhibitors include [R—(R*S*)]-5-chloro-N-[2-hydroxy-3-{methoxymethylamino}-3-oxo-1-(phenylmethyl) propyl-1H-indole-2-carboxamide and 5-chloro-1H-indole-2-carboxylic acid [(1S)-benzyl-(2R)-hydroxy-3-((3R,4S)-dihydroxy-pyrrolidin-1-yl-)-3-oxypropyl]amide; and specific examples of cholesteryl ester transfer protein (CETP) inhibitors include [2R,4S] 4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester, [2R,4S] 4-[acetyl-(3,5-bis-trifluoromethyl-benzyl)-amino]-2-ethyl-6-trifluoromethyl-3,4-dihydro-2H-quinoline-1-carboxylic acid isopropyl ester, [2R, 4S] 4-[(3,5-Bis-trifluoromethyl-benzyl)-methoxycarbonyl-amino]-2-ethyl-6-trifluoromethyl-3,4-dihydro-2H-quinoline-1-carboxylic acid isopropyl ester, the drugs disclosed in commonly owned U.S. patent application Ser. Nos. 09/918,127 and 10/066,091, both of which are incorporated herein by reference in their entireties for all purposes, and the drugs disclosed in the following patents and published applications: DE 19741400 A1; DE 19741399 A1; WO 994215 A1; WO 9914174; DE 19709125 A1; DE 19704244 A1; DE 19704243 A1; EP 818448 A1; WO 9804528 A2; DE 19627431 A1; DE 19627430 A1; DE 19627419 A1; EP 796846 A1; DE 19832159; DE 818197; DE 19741051; WO 9941237 A1; WO 9914204 A1; WO 9835937 A1; JP 11049743; WO 200018721; WO 200018723; WO 200018724; WO 200017164; WO 200017165; WO 200017166; EP 992496; and EP 987251, all of which are hereby incorporated by reference in their entireties for all purposes.

Polymers

Polymers suitable for use in the various aspects of the present invention should be pharmaceutically acceptable, and should have at least some solubility in aqueous solution at physiologically relevant pHs (e.g. 1-8). Almost any neutral or ionizable polymer that has an aqueous-solubility of at least 0.1 mg/mL over at least a portion of the pH range of 1-8 may be suitable.

It is preferred that the polymers be "amphiphilic" in nature, meaning that the polymer has hydrophobic and hydrophilic portions. Amphiphilic polymers are preferred because it is believed that such polymers tend to have relatively strong interactions with the drug and may promote the formation of various types of polymer/drug assemblies in solution. A particularly preferred class of amphiphilic polymers are those that are ionizable, the ionizable portions of such polymers, when ionized, constituting at least a portion of the hydrophilic portions of the polymer.

One class of polymers suitable for use with the present invention comprises neutral non-cellulosic polymers. Exemplary polymers include: vinyl polymers and copolymers having at least one substituent selected from the group comprising hydroxyl, alkylacyloxy, and cyclicamido; vinyl copolymers of at least one hydrophilic, hydroxyl-containing repeat unit and at least one hydrophobic, alkyl- or aryl-containing repeat unit; polyvinyl alcohols that have at least a portion of their repeat units in the unhydrolyzed (vinyl acetate) form; polyvinyl alcohol polyvinyl acetate copolymers; polyvinyl pyrrolidone; polyethylene polyvinyl alcohol copolymers, and polyoxyethylene-polyoxypropylene block copolymers (also referred to as poloxamers).

Another class of polymers suitable for use with the present invention comprises ionizable non-cellulosic polymers. Exemplary polymers include: carboxylic acid-functionalized vinyl polymers, such as the carboxylic acid functionalized polymethacrylates and carboxylic acid functionalized polyacrylates such as the EUDRAGITS® manufactured by Rohm Tech Inc., of Malden, Mass.; amine-functionalized polyacrylates and polymethacrylates; high molecular weight proteins such as gelatin and albumin; and carboxylic acid functionalized starches such as starch glycolate.

Non-cellulosic polymers that are amphiphilic are copolymers of a relatively hydrophilic and a relatively hydrophobic monomer. Examples include acrylate and methacrylate copolymers. Exemplary commercial grades of such copolymers include the EUDRAGITS, which are copolymers of methacrylates and acrylates.

A preferred class of polymers comprises ionizable and neutral (or non-ionizable) cellulosic polymers with at least one ester- and/or ether-linked substituent in which the polymer has a degree of substitution of at least 0.05 for each substituent. It should be noted that in the polymer nomenclature used herein, ether-linked substituents are recited prior to "cellulose" as the moiety attached to the ether group; for example, "ethylbenzoic acid cellulose" has ethoxybenzoic acid substituents. Analogously, ester-linked substituents are recited after "cellulose" as the carboxylate; for example, "cellulose phthalate" has one carboxylic acid of each phthalate moiety ester-linked to the polymer and the other carboxylic acid unreacted.

It should also be noted that a polymer name such as "cellulose acetate phthalate" (CAP) refers to any of the family of cellulosic polymers that have acetate and phthalate substituents attached via ester linkages to a significant fraction of the cellulosic polymer's hydroxyl groups. Generally, the degree of substitution of each substituent can range from 0.05 to 2.9 as long as the other criteria of the polymer are met. "Degree of substitution" refers to the average number of the three hydroxyls per saccharide repeat unit on the cellulose chain that have been substituted. For example, if all of the hydroxyls on the cellulose chain have been phthalate substituted, the phthalate degree of substitution is 3. Also included within each polymer family type are cellulosic polymers that have additional substituents added in relatively small amounts that do not substantially alter the performance of the polymer.

Amphiphilic cellulosics comprise polymers in which the parent cellulose polymer has been substituted at any or all of the 3 hydroxyl groups present on each saccharide repeat unit with at least one relatively hydrophobic substituent. Hydrophobic substituents may be essentially any substituent that, if substituted to a high enough level or degree of substitution, can render the cellulosic polymer essentially aqueous insoluble. Examples of hydrophobic substituents include ether-linked alkyl groups such as methyl, ethyl, propyl, butyl, etc.; or ester-linked alkyl groups such as acetate, propionate, butyrate, etc.; and ether- and/or ester-linked aryl groups such as phenyl, benzoate, or phenylate. Hydrophilic regions of the polymer can be either those portions that are relatively unsubstituted, since the unsubstituted hydroxyls are themselves relatively hydrophilic, or those regions that are substituted with hydrophilic substituents. Hydrophilic substituents include ether- or ester-linked nonionizable groups such as the hydroxy alkyl substituents hydroxyethyl, hydroxypropyl, and the alkyl ether groups such as ethoxyethoxy or methoxyethoxy. Particularly preferred hydrophilic substituents are those that are ether- or ester-linked ionizable groups such as carboxylic acids, thiocarboxylic acids, substituted phenoxy groups, amines, phosphates or sulfonates.

One class of cellulosic polymers comprises neutral polymers, meaning that the polymers are substantially non-ionizable in aqueous solution. Such polymers contain non-ionizable substituents, which may be either ether-linked or ester-linked. Exemplary ether-linked non-ionizable substituents include: alkyl groups, such as methyl, ethyl, propyl, butyl, etc.; hydroxy alkyl groups such as hydroxymethyl, hydroxyethyl, hydroxypropyl, etc.; and aryl groups such as phenyl. Exemplary ester-linked non-ionizable substituents include: alkyl groups, such as acetate, propionate, butyrate, etc.; and aryl groups such as phenylate. However, when aryl groups are included, the polymer may need to include a sufficient amount of a hydrophilic substituent so that the polymer has at least some water solubility at any physiologically relevant pH of from 1 to 8.

Exemplary non-ionizable cellulosic polymers that may be used as the polymer include: hydroxypropyl methyl cellulose acetate, hydroxypropyl methyl cellulose, hydroxypropyl cellulose, methyl cellulose, hydroxyethyl methyl cellulose, hydroxyethyl cellulose acetate, and hydroxyethyl ethyl cellulose.

A preferred set of non-ionizable (neutral) cellulosic polymers are those that are amphiphilic. Exemplary polymers include hydroxypropyl methyl cellulose and hydroxypropyl cellulose acetate, where cellulosic repeat units that have relatively high numbers of methyl or acetate substituents relative to the unsubstituted hydroxyl or hydroxypropyl substituents constitute hydrophobic regions relative to other repeat units on the polymer.

A preferred class of cellulosic polymers comprises polymers that are at least partially ionizable at physiologically relevant pH and include at least one ionizable substituent, which may be either ether-linked or ester-linked. Exemplary ether-linked ionizable substituents include: carboxylic acids, such as acetic acid, propionic acid, benzoic acid, salicylic acid, alkoxybenzoic acids such as ethoxybenzoic acid or propoxybenzoic acid, the various isomers of alkoxyphthalic acid such as ethoxyphthalic acid and ethoxyisophthalic acid, the various isomers of alkoxynicotinic acid such as ethoxynicotinic acid, and the various isomers of picolinic acid such as ethoxypicolinic acid, etc.; thiocarboxylic acids, such as thioacetic acid; substituted phenoxy groups, such as hydroxyphenoxy, etc.; amines, such as aminoethoxy, diethylaminoethoxy, trimethylaminoethoxy, etc.; phosphates, such as phosphate ethoxy; and sulfonates, such as sulphonate ethoxy. Exemplary ester linked ionizable substituents include: carboxylic acids, such as succinate, citrate, phthalate, terephthalate, isophthalate, trimellitate, and the various isomers of pyridinedicarboxylic acid, etc.; thiocarboxylic acids, such as thiosuccinate; substituted phenoxy groups, such as amino salicylic acid; amines, such as natural or synthetic amino acids, such as alanine or phenylalanine; phosphates, such as acetyl phosphate; and sulfonates, such as acetyl sulfonate. For aromatic-substituted polymers to also have the requisite aqueous solubility, it is also desirable that sufficient hydrophilic groups such as hydroxypropyl or carboxylic acid functional groups be attached to the polymer to render the polymer aqueous soluble at least at pH values where any ionizable groups are ionized. In some cases, the aromatic substituent may itself be ionizable, such as phthalate or trimellitate substituents.

Exemplary cellulosic polymers that are at least partially ionized at physiologically relevant pHs include: hydroxypropyl methyl cellulose acetate succinate (HPMCAS), hydroxypropyl methyl cellulose succinate, hydroxypropyl cellulose acetate succinate, hydroxyethyl methyl cellulose succinate, hydroxyethyl cellulose acetate succinate, hydroxypropyl methyl cellulose phthalate (HPMCP), hydroxyethyl methyl cellulose acetate succinate, hydroxyethyl methyl cellulose acetate phthalate, carboxyethyl cellulose, ethylcarboxymethyl cellulose (also referred to as carboxymethylethyl cellulose or CMEC), carboxymethyl cellulose, cellulose acetate phthalate (CAP), methyl cellulose acetate phthalate, ethyl cellulose acetate phthalate, hydroxypropyl cellulose acetate phthalate, hydroxypropyl methyl cellulose acetate phthalate, hydroxypropyl cellulose acetate phthalate succinate, hydroxypropyl methyl cellulose acetate succinate phthalate, hydroxypropyl methyl cellulose succinate phthalate, cellulose propionate phthalate, hydroxypropyl cellulose butyrate phthalate, cellulose acetate trimellitate (CAT), methyl cellulose acetate trimellitate, ethyl cellulose acetate trimellitate, hydroxypropyl cellulose acetate trimellitate, hydroxypropyl methyl cellulose acetate trimellitate, hydroxypropyl cellulose acetate trimellitate succinate, cellulose propionate trimellitate, cellulose butyrate trimellitate, cellulose acetate terephthalate, cellulose acetate isophthalate, cellulose acetate pyridinedicarboxylate, salicylic acid cellulose acetate, hydroxypropyl salicylic acid cellulose acetate, ethylbenzoic acid cellulose acetate, hydroxypropyl ethylbenzoic acid cellulose acetate, ethyl phthalic acid cellulose acetate, ethyl nicotinic acid cellulose acetate, and ethyl picolinic acid cellulose acetate. Of these cellulosic polymers that are at least partially ionized at physiologically relevant pHs, those that the inventors have found to be most preferred are HPMCAS, HPMCP, CAP, CAT, carboxyethyl cellulose, carboxymethyl cellulose, and ethyl carboxymethyl cellulose.

Another preferred class of polymers consists of neutralized acidic polymers. By "neutralized acidic polymer" is meant any acidic polymer for which a significant fraction of the "acidic moieties" or "acidic substituents" have been "neutralized"; that is, exist in their deprotonated form. By "acidic polymer" is meant any polymer that possesses a significant number of acidic moieties. In general, a significant number of acidic moieties would be greater than or equal to about 0.1 milliequivalents of acidic moieties per gram of polymer. "Acidic moieties" include any functional groups that are sufficiently acidic that, in contact with or dissolved in water, can at least partially donate a hydrogen cation to water and thus increase the hydrogen-ion concentration. This definition includes any functional group or "substituent," as it is termed when the functional group is covalently attached to a polymer that has a pKa of less than about 10. Exemplary classes of functional groups that are included in the above description include carboxylic acids, thiocarboxylic acids, phosphates, phenolic groups, and sulfonates. Such functional groups may make up the primary structure of the polymer such as for polyacrylic acid, but more generally are covalently attached to the backbone of the parent polymer and thus are termed "substituents." Neutralized acidic polymers are described in more detail in commonly assigned patent application U.S. Ser. No. 60/300, 256 entitled "Pharmaceutical Compositions of Drugs and Neutralized Acidic Polymers" filed Jun. 22, 2001, the relevant disclosure of which is incorporated by reference.

While specific polymers have been discussed as being suitable for use in the mixtures of the present invention, blends of such polymers may also be suitable. Thus the term "polymer" is intended to include blends of polymers in addition to a single species of polymer.

Concentration Enhancement

The polymer used in the compositions is preferably a "concentration-enhancing polymer," meaning that it meets at least one, and preferably both, of the following conditions. The first condition is that the concentration-enhancing polymer is present in a sufficient amount so as to increase the maximum drug concentration (MDC) of drug in the environment of use relative to a control composition consisting of an equivalent amount of crystalline drug in its lowest energy form but no polymer. That is, once the composition is introduced into an environment of use, the polymer increases the aqueous concentration of drug relative to the control composition. It is to be understood that the control composition is free from solubilizers or other components that would materially affect the solubility of drug, and that drug is in solid form in the control composition. The control composition is conventionally the undispersed, or crystalline form, of drug alone in its lowest energy, lowest solubility form. Preferably, the polymer increases the MDC of drug in aqueous solution by at least 1.25-fold relative to a control composition, more preferably by at least 2-fold, and most preferably by at least 3-fold. Surprisingly, the polymer may achieve extremely large enhancements in aqueous concentration. In some cases, the MDC of drug provided by the test composition is at least 5-fold to more than 10-fold the equilibrium concentration provided by the control.

The second condition is that the concentration-enhancing polymer is present in a sufficient amount so as to increase the dissolution area under the concentration versus time curve (AUC) of drug in the environment of use relative to a control composition consisting of an equivalent amount of crystalline drug in its lowest energy form but no polymer. (The calculation of an AUC is a well-known procedure in the pharmaceutical arts and is described, for example, in Welling, "Pharmacokinetics Processes and Mathematics," ACS Monograph 185 (1986).) More specifically, in the environment of use, the composition comprising drug and the concentration-enhancing polymer provides an AUC for any 90-minute period of from about 0 to about 270 minutes following introduction to the use environment that is at least 1.25-fold that of the control composition described above. Preferably, the AUC provided by the composition is at least 2-fold, more preferably at least 3-fold that of the control composition. For some dispersions, the test compositions of the present invention may provide an AUC value that is at least 5-fold, and even more than 10-fold that of a control composition as described above.

In a preferred embodiment, the concentration-enhancing polymer is present in a sufficient amount so that the composition provides concentration enhancement relative to a second control composition consisting of amorphous drug but no concentration-enhancing polymer. Preferably, the polymer increases at least one, and preferably both of the MDC or AUC of drug in aqueous solution by at least 1.25-fold relative to the second control composition, more preferably by at least 2-fold, and most preferably by at least 3-fold.

A "use environment" can be either an in vivo aqueous use environment, such as the GI tract of an animal, particularly a human, or an in vitro aqueous use environment of a test solution, such as phosphate buffered saline (PBS) solution or Model Fasted Duodenal (MFD) solution.

The resulting solid amorphous dispersions comprising a low-solubility drug and concentration-enhancing polymer formed using the processes of the present invention provide enhanced concentration of the dissolved drug in in vitro dissolution tests. It has been determined that enhanced drug concentration in in vitro dissolution tests in MFD solution or in PBS solution is a good indicator of in vivo performance and bioavailability. An appropriate PBS solution is an aqueous solution comprising 20 mM $Na_2HPO_4$, 47 mM $KH_2PO_4$, 87 mM NaCl, and 0.2 mM KCl, adjusted to pH 6.5 with NaOH. An appropriate MFD solution is the same PBS solution wherein there is also present 7.3 mM sodium taurocholic acid and 1.4 mM of 1-palmitoyl-2-oleyl-sn-glycero-3-phosphocholine. In particular, a composition formed by the inventive process can be dissolution-tested by adding it to MFD or PBS solution and agitating to promote dissolution.

An in vitro test to evaluate enhanced drug concentration in aqueous solution can be conducted by (1) adding with agitation a sufficient quantity of control composition, typically the undispersed drug alone, to the in vitro test medium, such as an MFD or a PBS solution, to achieve equilibrium concentration of drug; (2) in a separate vessel, adding with agitation a sufficient quantity of test composition (e.g., the composition comprising drug and polymer) in the same test medium, such that if all drug dissolved, the theoretical concentration of drug would exceed the equilibrium concentration of drug by a factor of at least 2, and preferably by a factor of at least 10; and (3) comparing the measured MDC and/or aqueous AUC of the test composition in the test medium with the equilibrium concentration, and/or with the aqueous AUC of the control composition. In conducting such a dissolution test, the amount of test composition or control composition used is an amount such that if all of the drug dissolved the drug concentration would be at least 2-fold, preferably at least 10-fold, and most preferably at least 100-fold that of the equilibrium concentration.

The concentration of dissolved drug is typically measured as a function of time by sampling the test medium and plotting drug concentration in the test medium vs. time so that the MDC can be ascertained. The MDC is taken to be the maximum value of dissolved drug measured over the duration of the test. The aqueous AUC is calculated by integrating the concentration versus time curve over any 90-minute time period between the time of introduction of the composition into the aqueous use environment (when time equals zero) and 270 minutes following introduction to the use environment (when time equals 270 minutes). Typically, when the composition reaches its MDC rapidly, in say less than about 30 minutes, the time interval used to calculate AUC is from time equals zero to time equals 90 minutes. However, if the AUC of a composition over any 90-minute time period described above meets the criterion of this invention, then the composition formed is considered to be within the scope of this invention.

To avoid large drug particulates that would give an erroneous determination, the test solution is either filtered or ceritrifuged. "Dissolved drug" is typically taken as that material that either passes a 0.45 μm syringe filter or, alternatively, the material that remains in the supernatant following centrifugation. Filtration can be conducted using a 13 mm, 0.45 μm polyvinylidine difluoride syringe filter sold by Scientific Resources (Scientific Resources, Inc; St. Paul, Minn.) under the trademark TITAN®. Centrifugation is typically carried out in a polypropylene microcentrifuge tube by centrifuging at 13,000 G for 60 seconds. Other similar filtration or centrifugation processes can be employed and useful results obtained. For example, using other types of microfilters may yield values somewhat higher or lower (±10-40%) than that obtained with the filter specified above but will still allow identification of preferred dispersions. It should be recognized that this definition of "dissolved drug" encompasses not only monomeric solvated drug molecules but also a wide range of species such as polymer/drug assemblies that have submicron dimensions such as drug aggregates, aggregates of mixtures of polymer and drug, micelles, polymeric micelles, colloidal particles or nanocrystals, polymer/drug complexes, and other such drug-containing species that are present in the filtrate or supernatant in the specified dissolution test.

Alternatively, the compositions, when dosed orally to a human or other animal, provide an AUC in drug concentration in the blood (serum or plasma) that is at least about 1.25-fold, preferably at least about 2-fold, preferably at least about 3-fold, preferably at least about 5-fold, and even more preferably at least about 10-fold that observed when a control composition consisting of an equivalent quantity of crystalline drug is dosed alone without any additional polymer. It is noted that such compositions can also be said to have a relative bioavailability of from about 1.25-fold to about 10-fold that of the control composition.

Relative bioavailability of drug in the compositions can be tested in vivo in animals or humans using conventional processes for making such a determination. An in vivo test, such as a crossover study, may be used to determine whether a composition of drug and concentration-enhancing polymer provides an enhanced relative bioavailability compared with a control composition as described above. In an in vivo crossover study a test composition of a solid amorphous dispersion of a drug and polymer is dosed to half a group of test subjects and, after an appropriate washout period (e.g., one week) the same subjects are dosed with a control composition that consists of an equivalent quantity of crystalline drug as the test composition (but with no polymer present). The other half of the group is dosed with the control composition first, followed by the test composition. The relative bioavailability is measured as the concentration in the blood (serum or plasma) versus time area under the curve (AUC) determined for the test group divided by the AUC in the blood provided by the control composition. Preferably, this test control ratio is determined for each subject, and then the ratios are averaged over all subjects in the study. In vivo determinations of AUC can be made by plotting the serum or plasma concentration of drug along the ordinate (y-axis) against time along the abscissa (x-axis). To facilitate dosing, a dosing vehicle may be used to administer the dose. The dosing vehicle is preferably water, but may also contain materials for suspending the test or control composition, provided these materials do not dissolve the composition or change the drug solubility in vivo.

Other features and embodiments of the invention will become apparent from the following examples which are given for illustration of the invention rather than for limiting its intended scope.

Example 1

This example demonstrates an improved process for forming an amorphous dispersion of a drug in a concentration-enhancing polymer. Drug 1 is [2R,4S] 4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester, also known as torcetrapib, and is shown by the following structure:

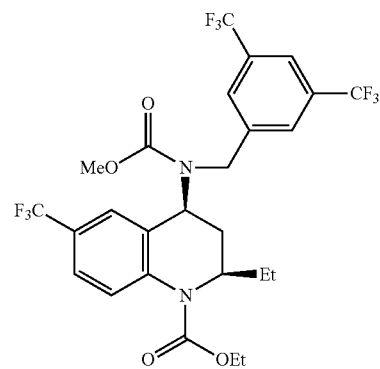 [SMILES: CCOC(=O)N1c2ccc(C(F)(F)F)cc2[C@@H](N(Cc2cc(C(F)(F)F)cc(C(F)(F)F)c2)C(=O)OC)C[C@H]1CC]

The dispersion was made by forming a spray solution containing 4 wt % Drug 1 and 12 wt % hydroxypropyl methyl cellulose acetate succinate (HPMCAS) (AQUOT-MG available from Shin Etsu, Tokyo, Japan) in acetone. The spray solution had a viscosity of about 130 cp. The spray solution was pumped using a high-pressure pump to a spray drier (Niro type XP Portable Spray Drier with a Liquid-Feed Process Vessel [PSD-1]) equipped with a pressure nozzle (Spraying Systems SK 80-16). The PSD-1 was also equipped with a 9-inch chamber extension and having for a gas disperser a diffuser plate having a 1% open area. The nozzle sat flush with the diffuser plate during operation. The spray solution was pumped to the spray drier at about 280 g/min, with an atomization pressure of 550 psi. Drying gas (nitrogen) entered the gas disperser at an inlet temperature of 132° C., and a flow rate of 1280 g/min. The evaporated solvent and wet drying gas exited the spray drier at the outlet at an outlet temperature of 37° C. The spray-dried dispersion formed by this process was collected in a cyclone, and the wet drying gas exited to a baghouse, then to a condenser, followed by a process heater, and then recirculated back into the spray-drying chamber. The condenser outlet temperature was −18° C.

The properties of the solid amorphous dispersion after spray drying were as follows:

TABLE 1

| Bulk Properties | Value |
| --- | --- |
| Bulk Specific Volume (cc/g) | 4.1 |
| Tapped Specific Volume (cc/g) | 2.6 |
| Hausner Ratio | 1.58 |
| Mean Particle Diameter (μm) | 50 |
| $D_{10}$, $D_{50}$, $D_{90}$* (μm) | 16.4, 45.8, 90.1 |
| Span $(D_{90} - D_{10})/D_{50}$ | 1.6 |
| Residual Acetone | 4.5% |

*10 vol % of the particles have a diameter that is smaller than $D_{10}$; 50 vol % of the particles have a diameter that is smaller than $D_{50}$, and 90 vol % of the particles have a diameter that is smaller than $D_{90}$.

Examples 2-4

Examples 2-4 were spray-dried using a PSD-1 with recirculated drying gas, as described for Example 1. The dispersions were made by forming spray solutions containing 4 wt % Drug 1 and 12 wt % HPMCAS in acetone, and spray drying these solutions with the operating conditions shown in Table 2.

TABLE 2

| Example | Drying gas flow (g/min) | Liquid feed rate (g/min) | Nozzle pressure (psi) | Inlet Temp. (° C.) | Outlet Temp. (° C.) | Condenser Outlet Temp. (° C.) | Acetone Partial Pressure (mmHg) |
| --- | --- | --- | --- | --- | --- | --- | --- |
| 1 | 1280 | 280 | 550 | 132 | 37 | −18 | 25.0 |
| 2 | 1277 | 280 | 550 | 133 | 39 | −9.4 | 41.8 |
| 3 | 1260 | 280 | 550 | 130 | 38 | −1.2 | 65.8 |
| 4 | 1270 | 280 | 550 | 134 | 39 | 8.9 | 110.3 |

The properties of the solid amorphous dispersions after spray drying were as follows (Example 1 is shown again for comparison):

TABLE 3

| Bulk Properties | Ex. 1 | Ex. 2 | Ex. 3 | Ex. 4 |
| --- | --- | --- | --- | --- |
| Bulk Specific Volume (cc/g) | 4.1 | 4.0 | 3.9 | 3.8 |
| Tapped Specific Volume (cc/g) | 2.6 | 2.6 | 2.4 | 2.4 |
| Hausner Ratio | 1.58 | 1.54 | 1.63 | 1.58 |
| Mean Particle Diameter (μm) | 50 | 49.2 | 45.7 | 46.2 |
| $D_{10}$, $D_{50}$, $D_{90}$ (μm) | 16.4, 45.8, 90.1 | 16.3, 44.9, 88.9 | 14.6, 41.6, 83 | 15.6, 42.2, 83.1 |
| Span $(D_{90} - D_{10})/D_{50}$ | 1.6 | 1.6 | 1.6 | 1.6 |
| Residual Acetone | 4.5% | 3.4% | 3.1% | 4.8% |

The data in Table 3 show that including a small amount of solvent vapor in the drying gas can lower the residual solvent level and specific volume of the solid amorphous dispersion particles. As shown in Table 3, the amount of residual solvent in the solid amorphous dispersion particles was lowest at a condenser outlet temperature of −1.2° C. (Example 3). At lower condenser outlet temperatures, and thus lower solvent vapor pressures in the drying gas, the residual solvent amount increases. Likewise, at a higher outlet condenser temperature of 8.9° C. (Example 4), the residual solvent level increases to 4.8 wt %. Thus, including a small amount of solvent vapor in the drying gas can yield a lower amount of residual solvent in the solid amorphous dispersions than using a dry drying gas. Specific volume of the solid amorphous dispersion particles also decreased with increasing amounts of solvent vapor in the drying gas.

Examples 5-6

These examples demonstrate an improved process for forming a solid amorphous dispersion of Drug 1 in a concentration-enhancing polymer, using a Niro PSD-2 portable spray-drier with recirculated drying gas. The solid amorphous dispersions were made by forming spray solutions containing 4 wt % Drug 1 and 12 wt % HPMCAS (AQUOT-MG available from Shin Etsu, Tokyo, Japan) in acetone, and mixing using a low shear impellar. The spray solutions were spray dried using a Niro PSD-2 drying chamber equipped with a pressure nozzle (Spraying Systems SK 70-27 with a 60° inverted cone face) and a DPH gas disperser from Niro, Inc. The spray conditions are shown in Table 4 below.

TABLE 4

| Example | Drying gas flow (m³/hr) | Liquid feed rate (kg/hr) | Nozzle pressure (psi) | Inlet Temp. (° C.) | Outlet Temp. (° C.) | Condenser Outlet Temp. (° C.) | Acetone Partial Pressure (mmHg) |
|---|---|---|---|---|---|---|---|
| 5 | 530 | 70 | 700 | 115 | 40 | −20 | 22.0 |
| 6 | 560 | 70 | 700 | 102 | 40 | 0 | 70.1 |

The properties of the solid amorphous dispersions after spray drying were as follows:

TABLE 5

| Bulk Properties | Exp 5 | Exp 6 |
|---|---|---|
| Bulk Specific Volume (cc/g) | 4.2 | 3.9 |
| Tapped Specific Volume (cc/g) | 2.5 | 2.3 |
| Hausner Ratio | 1.68 | 1.70 |
| Mean Particle Diameter (μm) | 74 | 77 |
| $D_{10}$, $D_{50}$, $D_{90}$ (μm) | 26, 67, 134 | 23, 64, 131 |
| Span $(D_{90} - D_{10})/D_{50}$ | 1.60 | 1.68 |
| Residual Acetone | 5.4% | 3.5% |

Examples 0.5 and 6 show again that as condenser outlet temperature is increased from −20° C. to 0° C. (Example 5 to Example 6), the increase in acetone vapor concentration in the drying gas leads to a reduction in residual solvent and bulk specific volume.

Example 7

A spray solution comprising 4 wt % Drug 1, 12 wt % of the polymer hydroxypropyl methyl cellulose acetate succinate, and 84 wt % of the solvent acetone is sprayed using the spray drying system of Example 5. The nozzle pressure is maintained from 500 to 800 psi, preferably from 600 to 700 psi. The pressure in the drying chamber is maintained in a range from 175 to 325 mmWC, preferably 225 to 325 mmWC. The temperature of the drying gas entering the dryer inlet is heated to a temperature at the inlet of from 90 to 150° C., preferably from 100 to 130° C. The feed rate of the spray solution is set at from 50 to 85 kg/hr, more preferably from 60 to 75 kg/hr. The drying gas flow rate is set at from 400 to 500 m³/hr, preferably from 470 to 480 m³/hr. The inlet temperature and spray solution feed rate are controlled to maintain an outlet temperature of from 35 to 45° C., preferably from 38 to 42° C. The solid amorphous dispersion particles are collected in a cyclone having a differential pressure of from 90 to 170 mmWC, preferably from 110 to 150 mmWC. The drying gas is recirculated through a condenser, and the condenser outlet temperature is maintained at from −30 to 0° C., preferably from −25 to −15° C.

Example 8

A spray solution comprising 4 wt % Drug 1, 12 wt % of the polymer hydroxypropyl methyl cellulose acetate succinate, and 84 wt % of the solvent acetone is sprayed into drying chamber having a volume of about 21 m³. The atomizer is a pressure nozzle having an internal wall defining a tapered cone shaped surface adjacent to the exit orifice.

The nozzle pressure is maintained from about 2,000 to about 3,000 psi. The pressure in the drying chamber is maintained in a range from about 0 to 800 mmWC. The temperature of the drying gas entering the dryer inlet is heated to a temperature at the inlet of from 100 to 200° C., preferably from 120 to 160° C. The feed rate of the spray solution is set at from 400 to 500 kg/hr. The drying gas flow rate is set at from 2000 to 2500 m³/hr. The inlet temperature and spray solution feed rate are controlled to maintain an outlet temperature of from 35 to 45° C., preferably from 38 to 42° C. The solid amorphous dispersion particles are collected in a cyclone. The drying gas is recirculated through a condenser, and the condenser outlet temperature is maintained at from −30 to 0° C., preferably from −25 to −15° C.

The invention claimed is:

1. A process for forming a pharmaceutical composition comprising a solid amorphous dispersion comprising a low-solubility drug and a polymer, comprising the steps of:
   (a) providing a drying apparatus having an atomizer in fluid communication with a drying chamber, said drying chamber having an Inlet and an outlet;
   (b) forming a spray solution by dissolving said low-solubility drug and said polymer in a solvent, wherein said polymer is an amphiphilic polymer;
   (c) spraying said spray solution through said atomizer into said drying chamber to form droplets having a volume average size of less than 500 μm;
   (d) flowing a drying gas through said inlet at a flow rate and a temperature $T_{IN}$ such that (i) said droplets solidify in less than about 20 seconds to form said solid amorphous dispersion of said low-solubility drug and said polymer, and (ii) a solvent vapor-laden drying gas is formed and exhausted from said outlet;
   (e) removing solvent vapor from said exhausted solvent vapor-laden drying gas to form a solvent vapor-depleted drying gas containing from 5 to about 25 wt % of said solvent in vapor form; and
   (f) directing said solvent vapor-depleted drying gas to said inlet so as to combine it with said drying gas,
wherein the feed rate of said spray solution is at least 10 kg/hr, said feed rate of said spray solution and $T_{IN}$ of said drying gas are controlled so that said drying gas at said outlet has a temperature $T_{OUT}$ that is less than the boiling point of said solvent, and wherein said solid amorphous dispersion is substantially homogenous, said $T_{OUT}$ is less than the glass transition temperature of said solid amorphous dispersion, and wherein the bulk specific volume of said dispersion is less than the bulk specific volume of a dispersion made with no solvent vapor in said drying gas.

2. The process of claim 1 wherein $T_{OUT}$ is at least 5° C. less than said boiling point of said solvent.

3. The process of claim 1 wherein $T_{OUT}$ is at least 10° C. greater than a dewpoint of said solvent in said drying chamber.

4. The process of claim 1 wherein said ratio of said flow rate of said drying gas to said spray solution feed rate is at least 4 m³/kg.

5. The process of claim 1 wherein said spray solution has a feed rate of at least 200 kg/hr.

6. The process of claim 1 wherein $T_{IN}$ ranges from 90 to 130° C. and $T_{OUT}$ ranges from 35 to 45° C.

7. The process of claim 1 wherein said solid amorphous dispersion has a residual solvent content of less than 10 wt % and a bulk specific volume of less than 5 cc/g.

8. The process of claim 1 wherein said amphiphilic polymer s selected from the group consisting of hydroxypropyl methyl cellulose acetate succinate (HPMCAS), hydroxypropyl methyl cellulose (HPMC), hydroxypropyl methyl cellulose phthalate (HPMCP), carboxy methyl ethyl cellulose (CMEC), cellulose acetate phthalate (CAP), and cellulose acetate trimellitate (CAT).

\* \* \* \* \*

UNITED STATES PATENT AND TRADEMARK OFFICE
CERTIFICATE OF CORRECTION

PATENT NO. : 10,383,941 B2
APPLICATION NO. : 10/910115
DATED : August 20, 2019
INVENTOR(S) : Beyerinck et al.

Page 1 of 1

It is certified that error appears in the above-identified patent and that said Letters Patent is hereby corrected as shown below:

In the Specification

Column 9, Line 41, "Good salvation also" should read --Good solvation also--.

In the Claims

Column 37, Line 7, "polymer s selected" should read --polymer is selected--.

Signed and Sealed this
Thirteenth Day of July, 2021

Drew Hirshfeld
*Performing the Functions and Duties of the*
*Under Secretary of Commerce for Intellectual Property and*
*Director of the United States Patent and Trademark Office*